United States Patent
Shivanand et al.

(10) Patent No.: US 6,346,270 B1
(45) Date of Patent: Feb. 12, 2002

(54) PHENYTOIN THERAPY

(75) Inventors: Padmaja Shivanand, Mountain View; Zahedeh Hatamkhany; Barbara F. Laidlaw, both of San Jose; Atul D. Ayer, Palo Alto, all of CA (US)

(73) Assignee: Alza Corporation, Mountain View, CA (US)

( * ) Notice: Subject to any disclaimer, the term of this patent is extended or adjusted under 35 U.S.C. 154(b) by 0 days.

(21) Appl. No.: 09/587,686

(22) Filed: Jun. 5, 2000

Related U.S. Application Data (62) Division of application No. 09/119,382, filed on Jul. 20, 1998, now Pat. No. 6,110,499.
(60) Provisional application No. 60/053,627, filed on Jul. 24, 1997.

(51) Int. Cl.$^7$ .................................................. A61K 9/24
(52) U.S. Cl. ....................... 424/473; 424/464; 424/465; 424/468; 424/484; 424/486; 424/472
(58) Field of Search ................................. 424/400, 464, 424/465, 468, 484, 486

(56) References Cited

U.S. PATENT DOCUMENTS

| | | | |
|---|---|---|---|
| 4,533,670 A | * | 8/1985 | Robertson |
| 4,795,644 A | * | 1/1989 | Zentner |
| 4,925,860 A | * | 5/1990 | Herbranson et al. |
| 5,366,738 A | * | 11/1994 | Rork et al. |
| 5,660,861 A | * | 8/1997 | Jao et al. |

* cited by examiner

Primary Examiner—Thurman K. Page
Assistant Examiner—P. E. McQueeney
(74) Attorney, Agent, or Firm—D. Byron Miller; Samuel E. Webb (57) ABSTRACT

A therapeutic composition, a dosage form and a method are disclosed for administering phenytoin indicated for the management of epilepsy.

4 Claims, 4 Drawing Sheets

PHENYTOIN THERAPY

REFERENCE TO RELATED APPLICATION

Benefit is claimed of Provisional application 60/053,627 filed Jul. 24, 1997 under 35 U.S.C. §119(e). This application is a division of U.S. Ser. No. 09/119,382, filed Jul. 20, 1998, now U.S. Pat. No. 6,110,499.

FIELD OF THE INVENTION

This invention pertains to both a novel and useful dosage form comprising phenytoin for the management of epilepsies. The invention relates also to a therapeutic composition of matter comprising phenytoin and a solubility enhancing agent. The invention relates also to a process for increasing the solubility of phenytoin in a therapeutic phenytoin formulation. Additionally, the invention pertains to a method for producing antiepileptic therapy in a patient in need of antiepileptic phenytoin therapy over time.

BACKGROUND OF THE INVENTION

The term "epilepsies" is a collective designation for a group of central nervous system disorders having in common the repeated occurrence of sudden and transitory episodes of abnormal phenomena of motor, convulsive, sensory, autonomic or psychic origin. The seizures are nearly always correlated with abnormal and excessive discharges in the brain, which can be recorded by an electroencephalogram.

Epilepsy is the most common neurological disorder. Epilepsy afflicts millions of people world wide, and it is more common in children than in adults. For the purposes of drug treatment, it is useful to classify patients according to the type of seizure the patient experiences. The generally accepted classification of epileptic seizure comprises partial seizures consisting of focal and local seizures, and generalized seizures consisting of convulsive or nonconvulsive seizures.

Partial seizures are classified further as simple partial seizures, complex partial seizures, and partial seizures secondarily generalized. Generalized seizures are classified further as absence seizures, atypical absence seizures, tonic-clonic and atonic seizures. The epilepsies are presented in *The Pharmacological Basis of Therapeutics,* 8th Ed., Goodman and Rall, editors. Pergamon Press publishers. Ch. 19.

The antiepileptic drug phenytoin and its alkali metal salts as represented by lithium, sodium and potassium, are known for treating epilepsies, as disclosed in *Pharmaceutical Sciences,* Remington, 18th Ed., Mack Publishing Co. 1990. pp. 1078. Therapeutically, phenytoin and its pharmaceutically acceptable salts are considered a drug of choice for the management of generalized tonic-clonic (grand mal) seizures, complex partial (temporal lobe psychomotor) seizures and simple partial (focal) seizures.

While phenytoin and its alkali salts are indicated for treating epilepsies, there are serious shortcomings associated with this drug. For example, phenytoin is poorly soluble in aqueous fluids, and this property makes it difficult to both provide and deliver it from a dosage form in a known dose over an extended time. For a dosage form that operates by osmotic imbibition, this poor solubility leads away from an osmotic dosage form and controlled delivery. The drug leads away as it lacks the required physical-chemical property needed to provide an osmotic gradient for imbibing fluid into the dosage form. Then too, since phenytoin is practically insoluble in an aqueous fluid, a high-loading dose must be housed in a dosage form that results in an unacceptably large dosage form and this precludes its oral use.

Prior to this invention, antiepileptic drugs were administered in conventional forms, such as a nonrate-controlling, dose-dumping capsule, or a nonrate-controlling, dose-dumping tablet, or by a dose-dumping capsule, and usually at multiple, repetitive dosing intervals. This prior-art mode of therapy lead to an initial high dose of drug in the blood, followed by a decreased dose of drug in the blood. The concentration differences in dosing patterns are related to the presence and absence of administered drug, which is a major disadvantage associated with conventional dosage forms. Conventional dosage forms and their mode of operation, including dose peaks and valleys, are discussed in *Pharmaceutical Sciences,* Remington, 18th Ed., 1990, Mack Publishing Co. pp. 1676–1686; *The Pharmaceutical and Clinical Pharmacokinetics,* 3rd Ed., 1984, Lea and Febiger, Philadelphia, pp. 1–28; and in U.S. Pat. Nos. 3,598,122 and 3,598,123, both issued to Zaffaroni.

The above presentation dictates of the critical need for a dosage form that overcomes the shortcomings of conventional dosage forms, including tablets, capsules, elixirs and suspensions. These conventional dosage forms and their accompanying peaks and valleys do not provide for dosage-regulating drug therapy over an extended period of time. The antiepileptic drugs as delivered by the prior art are dosed twice or thrice a day, which does not lend itself to controlled and sustained therapy. This prior-art pattern of drug administration speaks of the need for a dosage form that can administer the drug in a rate-controlled pattern over an extended time to provide constant therapy and thereby eliminate the peaks, valleys and multiple, uncontrolled dosing of the drug.

The prior art provides controlled-release dosage forms for administering a drug continuously over time. Representative of these dosage forms are disclosed in U.S. Pat. No. 4,327,725, issued to Cortese and Theeuwes; and in U.S. Pat. Nos. 4,612,008, 4,765,989 and 4,783,337, issued to Wong, Barclay, Deters and Theeuwes. The dosage forms disclosed in these patents provide a controlled release of drug over a prolonged time for constant drug therapy and they eliminate the need for multiple dosing of a drug. These dosage forms can deliver many drugs for their intended therapy, but there are certain drugs that are not readily delivered from these dosage forms. For example, the antiepileptic drug phenytoin is poorly soluble in aqueous fluids and this property, coupled with the dose needed for therapy, makes for difficult manufacturing, and the dosage form too large for acceptable therapy.

It is immediately apparent in light of the above presentation that an urgent need exists for a dosage form endowed with controlled-release delivery for administering the antiepileptic drug phenytoin for its therapy. The need exists for a dosage form for delivering phenytoin in a controlled-sustained therapeutically effective phenytoin dose for providing extended therapy. The need exists also for a therapeutic composition comprising a dose of phenytoin, and for a method for administering a dose of phenytoin to a patient. It will be appreciated by those versed in the antiepileptic-medicinal art that if the above are made available they would represent a major advancement in the therapy of epilepsies.

OBJECTS OF THE INVENTION

Accordingly, in view of the above presentation it is an immediate object of this invention to provide a dosage form for delivering phenytoin for treating epilepsies which dosage form overcomes the shortcomings known to the prior art.

Another object of the present invention is to provide a dosage form that delivers phenytoin in a continuous release over time.

Another object of the invention is to provide a dosage form for administering phenytoin in a controlled rate and therapeutic dose over an extended period of time.

Another object of the invention is to provide a dosage form housing an increased dose of phenytoin for epilepsy management.

Another object of the invention is to provide a pharmaceutically acceptable composition of matter comprising a dose of phenytoin for the management of epilepsies in patients in need thereof.

Another object of the invention is to provide a therapeutic composition comprising phenytoin and a solubility enhancing agent to increase the phenytoin concentration in the composition, and available for therapy.

Another object of the invention is to provide a therapeutic composition comprising phenytoin and an agent that increases the solubility of phenytoin, thereby increasing the hydration of the drug so a higher dose of phenytoin can be incorporated into a dosage form.

Another object of the invention is to provide a phenytoin formulation that delivers in a controlled-continuous release dose phenytoin to a patient in need of phenytoin for maintaining an antiepileptic phenytoin level in the blood as a function of the phenytoin-releasing formulation.

Another object of the invention is to provide a dosage form that reduces and/or eliminates the unwanted influences of a gastrointestinal environment on the delivery of phenytoin from a dosage form in the gastrointestinal tract.

Another object of the invention is to provide a dosage form that delivers phenytoin orally to a patient in need of antiepileptic phenytoin therapy.

Another object of the invention is to provide a method for the prevention and for the control of epileptic seizures by administering phenytoin to a human patient afflicted with same.

Another object of the invention is to provide a method for the administration of phenytoin by orally administering phenytoin in a dose per unit time over an extended time to establish a plasma phenytoin concentration in a patient in need of antiepileptic phenytoin therapy.

Another object of the invention is to provide a therapeutic composition comprising phenytoin blended with a pharmaceutically acceptable polymer and with a solubility enhancer.

Another object of the invention is to provide a dosage form comprising an external coat of phenytoin for instant phenytoin therapy.

Other objects, features and advantages of the invention will be more apparent to those versed in the dispensing art from the accompanying detailed specification taken in conjunction with the accompanying claims.

BRIEF DESCRIPTION OF THE DRAWINGS

In the drawing figures, which are not drawn to scale, but are set forth to illustrate various embodiments of the invention, the drawing figures are as follows.

Drawing

Drawing

Drawing

Drawing

Drawing

Drawing

Drawing

Other objects, features and advantages of the invention will be more apparent to those versed in the dispensing art from the accompanying specification, taken in conjunction with the drawing figures and the claims.

DETAILED DESCRIPTION OF DRAWINGS

Figure 1:
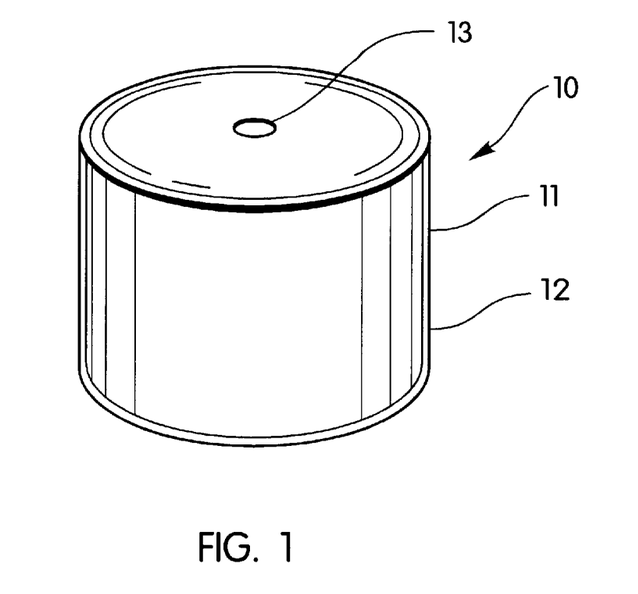
FIG. 1 is a general view of a dosage form provided by this invention, designed and shaped for the oral administration of phenytoin for the treatment of epilepsies at a controlled rate over time to a patient in need of therapy for the management of epilepsies.

Turning now to the drawing figures in detail, which drawing figures are examples of dosage form provided by this invention, and which examples are not to be construed as limiting, one example of a dosage form is seen in drawing FIG. 1. In drawing FIG. 1, a dosage form 10 is seen comprised of a body member 11, which body 11 comprises wall 12. Wall 12 is an exterior wall and it surrounds and forms an internal area, not seen in drawing FIG. 1. Drawing FIG. 1 comprises at least one exit 13 that connects the exterior of drawing FIG. 1 with the interior of dosage form 10.

The dosage form 10 of drawing FIG. 1 illustrates a controlled-release dosage form that delivers phenytoin over an extended time. The phrase "controlled-release" denotes that the dosage form controls the delivery of phenytoin at a controlled-rate per unit time over an extended time of ½ up to 25 hours. The dosage form provided by this invention is useful for maintaining therapeutic phenytoin levels in the blood, including blood plasma. The dosage form as seen in drawing FIG. 1 embraces the shape of a tablet, and it could embrace the shape of a capsule and other oral dosage forms. The extended-continuous time of delivery for the dosage form denotes a delivery time greater than conventional, noncontrolled tablets and noncontrolled capsules that exhibit dose-dumping of their drug.

Figure 2:
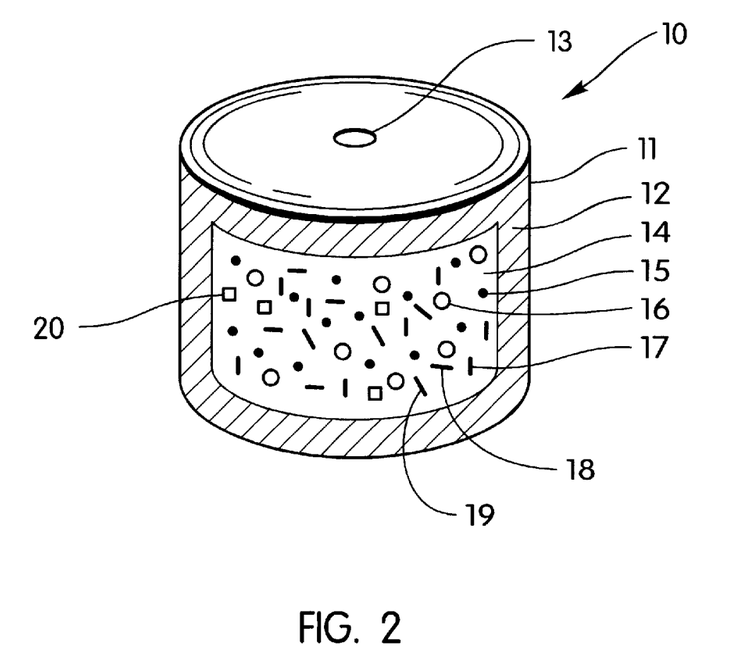
FIG. 2 is an opened view of drawing FIG. 1, depicting a dosage form of the invention comprising an internal pharmaceutically acceptable composition comprising phenytoin indicated for the management of epilepsies.

In drawing FIG. 2, dosage form 10 is seen in opened-section with a section of its wall 12 removed for illustrating the internal area 14 of dosage form 10. In drawing FIG. 2, dosage form 10 comprises body 11, wall 12, exit passageway 13, and internal area 14, also identified as internal compartment 14. Wall 12, which surrounds and defines internal compartment 14, comprises totally or in at least a part a semipermeable composition. The semipermeable composition is permeable to the passage of an exterior fluid, such as an aqueous fluid, and it is permeable to biological fluid present in the gastrointestinal tract. Wall 12 is nontoxic and it is impermeable to the passage of antiepileptic phenytoin 15, represented by dots, present in compartment 14. Wall 12 is inert, and it maintains its physical and chemical integrity during the dispensing life of antiepileptic phenytoin 15. The phrase "maintains its physical and chemical integrity" means wall 12 does not lose its structure and it does not undergo chemical change during the dispensing of phenytoin 15.

Wall 12 comprises a composition that does not adversely affect an animal, a human, or components of the dosage form. Compositions for forming wall 12 are, in one embodiment, comprised of a member selected from the group consisting of a cellulose ester polymer, a cellulose ether polymer and a cellulose ester-ether polymer. These cellulosic polymers have a degree of substitution, DS on the anhydroglucose unit, from greater that 0 up to 3 inclusive. By "degree of substitution" is meant the average number of hydroxyl groups originally present on the anhydroglucose unit comprising the cellulose polymer that are replaced by a substituting group. Representative wall 12 polymers comprise a member selected from the group consisting of cellulose acylate, cellulose diacylate, cellulose triacylate, cellulose acetate, cellulose diacetate, cellulose triacetate, mono-, di- and tricellulose alkanylates, mono-, di and tricellulose aroylates, mono-, di- and tricellulose alkenylates, and mono-, di- and tricellulose alkinylates. Exemplary polymers include cellulose acetate having a DS of up to 1 and an acetyl content of up to 21%; cellulose acetate having a DS of 1 to 2 and an acetyl content of 21 to 35%; cellulose acetate having a DS of 2 to 3 and an acetyl content of 35 to 44.8%, and the like. More specific cellulosic polymers comprise cellulose propionate having a DS of 1.8, a propyl content of 39.2 to 45% and a hydroxyl content of 2.8 to 5.4; cellulose acetate butyrate having a DS of 1.8, an acetyl content of 13 to 15% and a butyryl content of 34 to 39%; cellulose acetate butyrate having an acetyl content of 2 to 29%, a butyryl content of 17 to 53% and a hydroxyl content of 0.5 to 4.7; cellulose triacylates having a DS of 2.9 to 3, such as cellulose trivalerate, cellulose trilaurate, cellulose tripalmitate, cellulose trisuccinate and cellulose trioctanoate; celluloses diaceylate having a DS of 2.2 to 2.6, such as cellulose disuccinate, dipalmitate, cellulose dioctanoate, cellulose dipentanoate, co-esters of cellulose, such as cellulose acetate butyrate and cellulose acetate propionate.

Additional semipermeable polymers comprise acetaldehyde dimethylcellulose acetate; cellulose acetate ethylcarbamate; cellulose acetate methylcarbamate; cellulose diacetate propylcarbamate; cellulose acetate diethylaminoacetate; semipermeable polyamide; semipermeable polyurethane; semipermeable sulfonated polystyrene; semipermeable crosslinked selective polymer formed by the coprecipitation of a polyanion and polycation, as disclosed in U.S. Pat. Nos. 3,173,876, 3,276,586, 3,541,005, 3,541,006 and 3,546,876; semipermeable polymers as disclosed by Loeb and Sourirajan in U.S. Pat. No. 3,133,132; semipermeable, lightly crosslinked polystyrenes; semipermeable crosslinked poly(sodium styrene sulfonate); semipermeable cross-linked poly(vinylbenzytrimethyl ammonium chloride); and semipermeable polymers possessing a fluid permeability of $2.5 \times 10^{-8}$ to $5 \times 10^{-3}$ (cm$^2$/hr·atm), expressed per atmosphere of hydrostatic or osmotic pressure difference across the semipermeable wall. The polymers are known to the polymer art in U.S. Pat. Nos. 3,845,770; 3,916,899 and 4,160,020; and in *Handbook of Common Polymers*, Scott, J. R. and W. J. Roff, 1971, CRC Press, Cleveland Ohio.

The dosage amount of phenytoin 15 in dosage form 10 is 1 to 750 mg. The phenytoin 15 is present in doses of, for example 1, 5, 30, 50, 100, 225, 300, and 400 up to 750 mg in compartment 14. The phenytoin can be delivered at a rate of 0.04 mg/hr up to 50 mg/hr to provide a blood plasma level of 0.1 to 20 µg/ml (micrograms/milliliter). The phenytoin 15 can be administered for adjunctive therapy with a different antiepileptic drug to epilepsy patients. Representative of adjunctive antiepileptic drugs that can be administered from dosage form 10 comprise phenytoin and phenobarbitone; phenytoin and carbamazepine; phenytoin and primidone; phenytoin and felbamate; phenytoin and gabapentin; phenytoin and mephenytoin; phenytoin and ethytoin and phenytoin and phenobarbital sodium. The dosage amount of adjunctive-antiepileptic therapy for each adjunctive drug is 1 to 375 mg, with the total dosage for adjunctive-antiepileptic therapy 2 to 750 mg.

A solubility enhancing agent 16, identified by circles, is present in compartment 14 for increasing the solubility and concomitantly the concentration of phenytoin, for example, sodium phenytoin in solution. The solubility enhancing agent maintains a high pH environment, for example, above pH seven to provide an alkaline environment for keeping the sodium phenytoin in solution. The enhancing agents as used for this invention increase the solubility of phenytoin at least six fold. Phenytoin is poorly soluble in aqueous fluid and a need exists for increasing its solubility for correspondingly increasing the dose of phenytoin that can be delivered without resulting in an unacceptably large delivery composition and/or dosage form, and precipitation of phenytoin. The solubility enhancing agents useful for this invention comprises a method selected from the group consisting of tromethamine; tris(hydroxymethyl)aminomethane; diethanolamine; glycineamide; triethanolamine; N-[tris-(hydroxymethyl)methyl]glycine; sodium acetate; sodium lactate; sodium glycocholate; sodium propionate; sodium butyrate; sodium glycoholate; glycocholate sodium phosphate; and sodium phosphate. The solubility enhancing agents function as an alkalinizing agent to maintain an alkaline environment. The amount of phenytoin solubility enhancing agent present in composition or dosage form is 1 to 75 mg.

Compartment 14 contains a pharmaceutically acceptable osmopolymer 17 carrier, represented by vertical dashes, homogenously blended with phenytoin 15. The osmopolymer 17 useful for this purpose is compatible with phenytoin. The osmopolymer aids in transporting phenytoin in a known dose to a patient. The osmopolymers comprise a member selected from the group consisting of a polyalkylene oxide possessing a 75,000 to 600,000 weight-average molecular weight, and a carboxyalkylcellulose possessing a 25,000 to 150,000 weight-average molecular weight. Representative of polyalkylene oxides comprise a polyethylene oxide of 100,000 molecular weight; a polyethylene oxide of 200,000 molecular weight; a polyethylene oxide of 300,000 molecular weight; a polypropylene oxide of 400,000 molecular weight and a polypropylene oxide of 600,000 molecular weight. Representative of carboxyalkylcellulose is alkali carboxyalkylcellulose, including sodium and potassium carboxymethylcellulose of 40,000 molecular weight, sodium carboxymethylcellulose of 75,000 molecular weight and sodium carboxymethylcellulose of 90,000 molecular weight. The antiepileptic composition comprising the phenytoin contains 30 to 400 mg of osmopolymer 17.

The antiepileptic composition comprising phenytoin comprises 1 to 60 mg of a phenytoin compatible binder, represented by polyvinylpyrrolidone 18, represented by horizontal dashes, possessing a 2,500 to 3,000,000 viscosity-average molecular weight; and/or in a further manufacturer the antiepileptic composition comprises 1 mg to 60 mg of hydroxypropylmethylcellulose of 9,200 to 225,000 numerical average molecular weight; which binder imparts cohesive qualities to the ingredients in the composition. The antiepileptic composition comprising phenytoin comprises 0.1 to 10 mg of a lubricant 19, represented by slanted dashes, which lubricant comprises a member selected from the group consisting of sodium stearate, magnesium stearate, stearic acid, calcium stearate, oleic acid, potassium oleate and caprylic acid; and 2.5 to 75 mg of an osmagent 20, represented by squares, selected from the group consisting of magnesium sulfate, magnesium chloride, sodium chloride, potassium chloride, lithium chloride, potassium sulfate, sodium sulfate, mannitol, sorbitol, inositol, glucitol, urea, sucrose, glucose, fructose and lactose. The osmagents, also known as osmotic agents, osmotically effective compounds and osmotic solutes, exhibit an osmotic pressure gradient across semipermeable wall 12 of 2.5 to 500 atmospheres. The osmagents imbibe aqueous fluid through wall 12 for hydro-osmotically delivering phenytoin from an osmotic dosage form.

Figure 3:
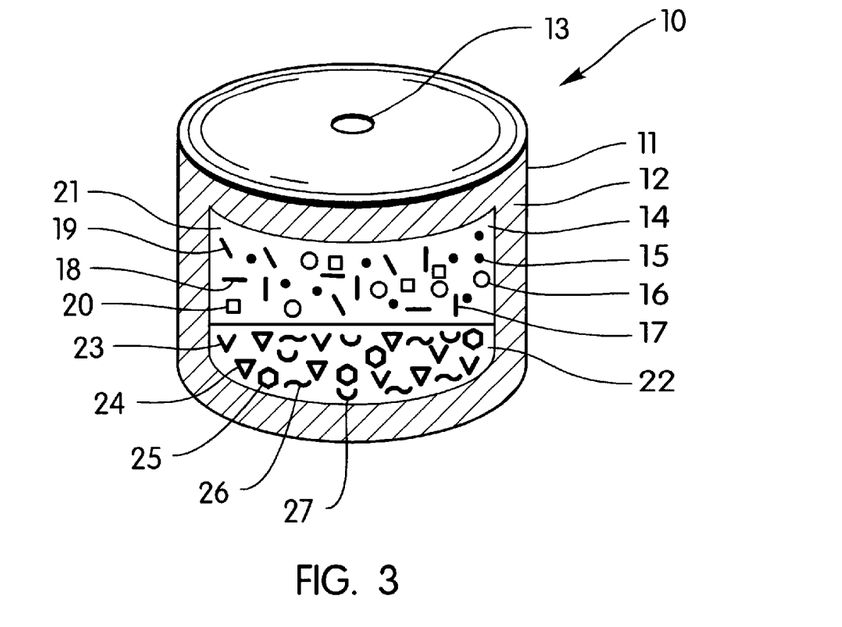
FIG. 3 is an opened view of drawing FIG. 1 illustrating a dosage form comprising a pharmaceutical phenytoin composition and a composition comprising means for pushing the pharmaceutical phenytoin composition from the dosage form.

In drawing FIG. 3, dosage form 10 is seen in opened view for illustrating internal compartment 14. Internal compartment 14 comprises the phenytoin composition described in detail in drawing FIG. 2. The phenytoin composition is identified in drawing FIG. 3 as phenytoin composition 21 or as phenytoin layer 21. Dosage form 10 in compartment 14 comprises an expandable composition 22, also identified as expandable layer 22. Expandable layer 22 cooperates with phenytoin layer 21 for delivering phenytoin 15 from dosage form 10.

Expandable layer 22 comprises 25 to 400 mg of an expandable osmopolymer 23, represented by V. The osmopolymer 23 comprise a member selected from the group consisting of polyalkylene oxide of 1,500,000 to 8,000,000 weight-average molecular weight. The osmopolymers 23 in expandable layer 22 possess a higher molecular weight than the osmopolymers in phenytoin layer 21. Representative of the polyalkylene oxides are polyethylene oxide of 2,000,000 molecular weight, polyethylene oxide of 5,000,000 molecular weight and polyethylene oxide of 7,500,000 molecular weight. Representative of carboxyalkylcellulose comprise the alkali sodium and potassium carboxyalkylcellulose, including sodium carboxymethylcellulose of 200,000 molecular weight, sodium carboxymethylcellulose of 1,250,000 molecular weight and sodium carboxymethylcellulose of 3,250,000 molecular weight. The osmopolymers used for the expandable layer exhibit an osmotic pressure gradient across semipermeable wall 12; they imbibe fluid into compartment 14; and, thereby expand and push the phenytoin from the osmotic dosage form. The amount of osmopolymer 23 in expandable layer 22 is 25 to 400 mg.

Expandable layer 22 comprises 5 to 100 mg of an osmotically active solute 24, represented by a triangle, also known as osmagent, for contributing to the delivery kinetics of phenytoin 15. Representative of osmotically active solute 24 is a member selected from the group consisting of sodium chloride, sorbitol, potassium chloride, magnesium sulfate, lithium phosphate, lithium chloride, sodium phosphate, potassium sulfate, sodium sulfate and potassium phosphate. Expandable layer 22 comprises 1 to 50 mg of a hydroxypropylalkylcellulose 25, or polyvinylpyrrolidone represented by a hexagonal. The hydroxypropylalkylcellulose possess a 9,000 to 400,000 number-average molecular weight comprising a member selected from the group consisting of hydroxypropylmethylcellulose, hydroxypropylethylcellulose, hydroxypropylisopropylcellulose, hydroxypropylbutylcellulose and hydroxypropylpentylcellulose. The poly(vinyl pyrrolidone) comprises 2,500 to 3,000,000 viscosity average molecular weight, represented by copolymer of poly(vinylpyrrolidone) with vinyl acetate, and copolymers of poly(vinyl-pyrrolidone) with vinyl laurate. Expandable layer 22 comprises 0 to 5 mg of a nontoxic colorant 26, identified by a wavy line. Colorant 26 includes Food and Drug Administration Colorants such as FD&C No. 1 blue dye and ferric oxide. A lubricant 27, identified by a half-circle, is formulated into expandable layer 22 and comprises a member selected from the group consisting of sodium stearate, potassium stearate, magnesium stearate, stearic acid, calcium stearate, calcium palmitate and potassium oleate. The concentration of lubricant 27 is 0.1 to 5 mg.

Figure 4:
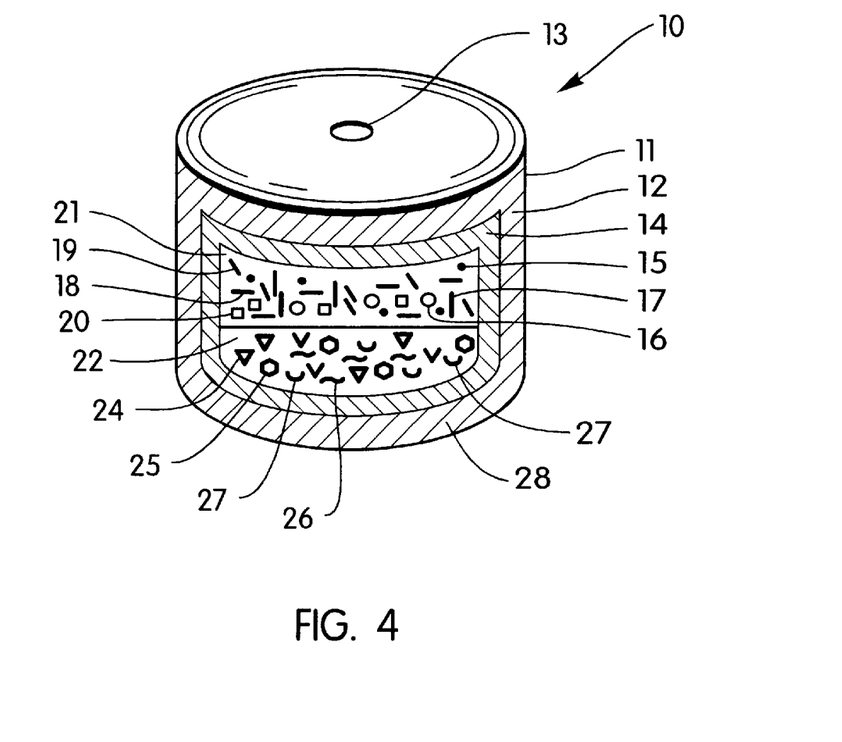
FIG. 4 is an opened view of drawing FIG. 1 depicting a dosage form provided by the invention comprising an internal wall and a subcoat, positioned between the internal surface of the wall of the dosage form and the pharmaceutical phenytoin composition and the composition for pushing the pharmaceutical composition from the dosage form.

Dosage form 10, as seen in drawing FIG. 4, depicts another dosage form provided by this invention. Dosage form 10 comprises an exterior wall 12 and an interior wall 28. Interior wall 28 has one surface in contacting relation with the interior surface of wall 12. The exterior surface of wall 12 faces the environment of use. Interior wall 28 defines the internal compartment 14, with interior wall 28 positioned around phenytoin layer 21 and expandable layer 22. The two walls 12 and 28 provide unexpected advantages as the two walls 12 and 28 operate to protect fluid-sensitive phenytoin from the unwanted influences of aqueous and biological fluids, wall 12 and 28 together protect phenytoin from direct contact with gastrointestinal pH of 1 to 7 while in the dosage form. Further, interior wall 28 provides structural support for exterior wall 12 and prevents and/or lessens the incidence of cracking of wall 12. Wall 28 in cooperation with wall 12 functions to maintain the integrity and the performance of dosage form 10. Interior wall 28 comprises 5 to 60 mg of a hydroxyalkylcellulose possessing a 10,000 to 1,500,000 viscosity-average molecular weight, and the hydroxyalkylcellulose are selected from the group consisting of hydroxymethylcellulose, hydroxyethylcellulose, hydroxypropylcellulose, hydroxybutylcellulose, hydroxypentylcellulose and hydroxyhexylcellulose. Wall 28 comprises 0.5 to 20 mg of a polyethylene glycol possessing 950 to 7,500 viscosity-average molecular weight. The polyethylene glycols as used herein are distinguished from polymers of alkylene oxide, and the polyethylene glycols do not embrace the polymers of alkylene oxide.

Figure 5:
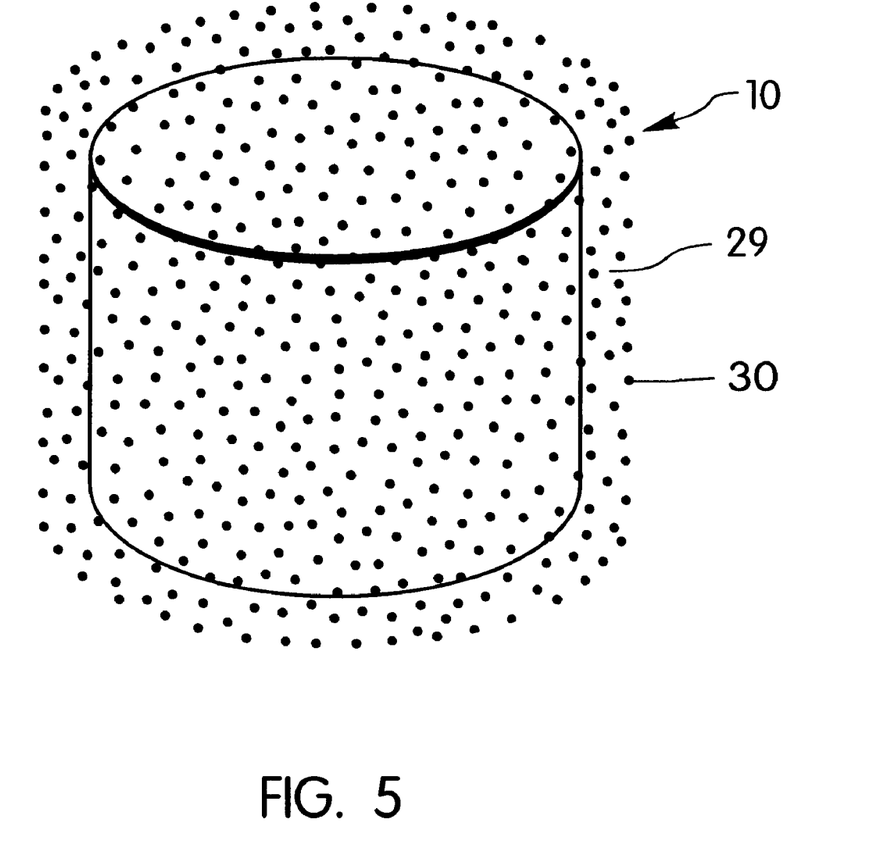
FIG. 5 is a view of a dosage form provided by the invention, which dosage form is illustrated comprising an instant-release overcoat on the exterior of the dosage form, which overcoat comprises an immediate dose of phenytoin for the management of epilepsies.
Figure 6:
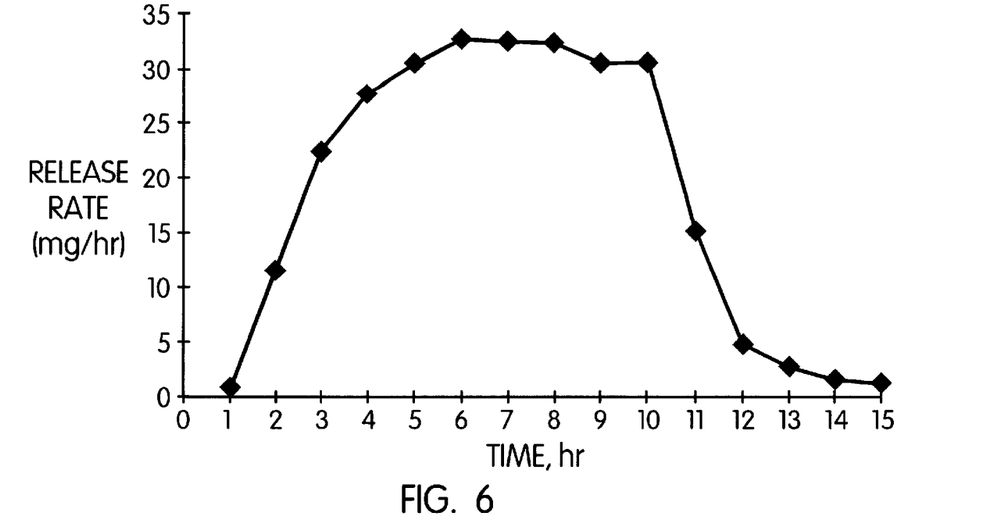
FIG. 6 illustrates the release rate in milligrams of sodium phenytoin over 15 hours by a dosage form provided by the invention.

Dosage form 10 as seen in drawing FIG. 5 depicts another manufacture provided by the invention. Dosage form 10 comprises an overcoat 29 on the outer surface of dosage form 10. The overcoat 29 is a therapeutic composition comprising 1 to 50 mg of phenytoin and a pharmaceutically acceptable carrier selected from the group consisting of alkylcellulose, hydroxyalkylcellulose and hydroxypropylalkylcellulose. Representative of the pharmaceutically acceptable carrier include methylcellulose, hydroxyethylcellulose, hydroxypropylcellulose, hydroxypropylmethylcellulose, hydroxypropylethylcellulose and hydroxypropylbutylcellulose. Overcoat 29 provides therapy immediately as overcoat 29 dissolves or undergoes dissolution in the presence of gastrointestinal fluid, and concurrently therewith delivers phenytoin on entrance into the gastrointestinal tract for immediate phenytoin therapy.

Dosage form 10, manufactured as an osmotically controlled-release dosage form, comprises at least one passageway 13. The phrase "controlled-release" as used herein indicates that control is exercised over both the duration and the profile of the antiepileptic-phenytoin release pattern. The expression "passageway" as used for the purpose of this invention includes aperture; orifice; bore; pore; porous element through which phenytoin drug 15 can be pumped, diffuse or migrate through a fiber; capillary tube; porous overlay; porous insert; microporous member and porous composition. The passageway includes also a compound that erodes or is leached from wall 12 in the fluid environment of use to produce at least one passageway. Representative compounds for forming a passageway include erodible poly(glycolic) acid or poly(lactic) acid in the wall; a gelatinous filament; a water-removable poly(vinyl alcohol); leachable compounds, such as fluid-removable pore-forming polysaccharides, acids, salts or oxides. A passageway can be formed by leaching a compound from the wall, such as sorbitol, sucrose, lactose, maltose or fructose, to form a controlled-release dimensional pore-passageway. The passageway can have any shape, such as round, triangular, square and elliptical, for assisting in the controlled-metered release of phenytoin from the dosage form. The dosage form can be manufactured with one or more passageways in spaced-apart relation on one or more surfaces of the dosage form. A passageway and equipment for forming a passageway are disclosed in U.S. Pat. Nos. 3,845,770 and 3,916,899 by Theeuwes and Higuchi; in U.S. Pat. No. 4,063,064 by Saunders, et al. and in U.S. Pat. No. 4,088,864 by Theeuwes, et al. Passageways comprising controlled-release dimensions sized, shaped and adapted as a releasing-pore formed by aqueous leaching to provide a releasing-pore of controlled-release rate are disclosed in U.S. Pat. Nos. 4,200,098 and 4,285,987 by Ayer and Theeuwes.

PROCESS FOR PROVIDING THE INVENTION

Wall 12 of dosage form 10 is manufactured in one process, comprising an air suspension process. This process consists in suspending and tumbling a compressed drug core, comprising a single-layered core or a bilayered core, in a current of air and wall-forming composition until a wall is applied to the single-layered core or the bilayered core. The air suspension procedure is well suited for independently forming the wall. The air suspension procedure is described in U.S. Pat. No. 2,799,241; *J Amer Pharm Assoc*, Vol. 48, pp. 451–454 (1959); and ibid., Vol. 49, pp. 82–84 (1960). Dosage form 10 can be coated also with a wall-forming composition in a Wurster® air suspension coater using methylene dichloride-methanol cosolvent, for example, 80:20 wt:wt, an ethanol-water, or acetone-water cosolvent, or a 95:5 wt:wt using 2.5 to 4% solids. An Aeromatic® air suspension coater using a methylene dichloride-methanol cosolvent, for example, 80:20 wt:wt, can be used for applying the wall. Other wall-forming techniques, such as a pan-coating system, wherein wall-forming compositions are deposited by successive spraying of the composition to provide a wall surrounding a compartment, accompanied by tumbling in a rotating pan can be used to provide the dosage form. Finally, the wall coated cores are dried in a forced-air oven at 30 to 50° C. for up to a week to free the dosage form of solvent. Generally, the walls formed by these techniques have a thickness of 1 to 30 mils (0.0254 to 0.762 mm).

Dosage form 10 of the invention is manufactured by general manufacturing techniques. For example, in one manufacture the drug and other core-forming ingredients comprising a single drug layer or bilayer core with drug facing the exit means 13 are blended and pressed into a solid layer, or a solid bilayer. The drug and other ingredients can be dry-blended or blended with a solvent and mixed into a solid or semisolid formed by conventional methods such as ball-milling, calendaring, stirring, roll-milling or churning, and then pressed into a preselected shape. The layer possesses dimensions that correspond to the internal dimensions of the area the layer occupies in the dosage form, and in a bilayer it also possesses dimensions corresponding to the second layer for forming a contacting arrangement therewith. In a bilayered core, the push layer is placed in contact with the drug layer. The push layer is manufactured using techniques for providing the drug layer. The layering of the drug layer and the push layer can be fabricated by conventional press-layering techniques. Finally, a single layer of the two-layer compartment-forming members are surrounded and coated with an exterior wall or with an interior and exterior wall. A passageway is laser or mechanically drilled through the wall to contact the drug layer. When the passageway is formed by a laser, the dosage form is optically-oriented automatically by the laser equipment for forming the passageway on the preselected surface for forming the passageway.

In another manufacture, dosage form 10 is manufactured by the wet granulation technique. Granulation is a process of size enlargement whereby small particles are gathered into larger aggregates or granules, as reported in *Encyclopedia of Pharmaceutical Technology* Vol. 7, pp 121–160, 1993. In the wet granulation technique, for example, the drug and the ingredients comprising the drug-forming layer or the drug-expandable layers are blended using a solvent, such as ethyl alcohol-water 98:2 v:v (volume:volume) as the granulation fluid. Other granulating fluid, such as denatured alcohol 100%, can be used for this purpose. The ingredients forming the drug core or layers are individually passed through a mesh screen, such as a U.S. Sieve Series screen, and then thoroughly blended in a mixer. Other ingredients comprising the layer or layers are dissolved in a portion of the granulation fluid, such as the cosolvent described above. Then, the latter-prepared wet blend is added slowly to the drug blend with continual mixing in the blender. The granulating fluid is added until a wet blend is produced, which wet mass is then forced through a mesh screen onto oven trays. The blend is dried for 18 to 24 hours at 30 to 50° C. The dry granules are sized then with a mesh screen. Next, a lubricant is passed through a screen and added to the dry screened granule blend. The granulation is placed in a blender and blended for 1 to 15 minutes.

A push layer is made by the same wet granulation procedure, which consists in suspending and tumbling the two contacting layers in a current of air. Then, the layers are surrounded with a wall-forming composition. The delivery system provided by this invention are generally manufactured in a controlled humidity environment consisting of a relative humidity of less than 40%. The air suspension procedure is described in U.S. Pat. No. 2,799,241; *J Amer Pharm Assoc*, Vol. 48, pp. 451–454 (1979); and ibid., Vol. 49, pp. 82–84 (1960). Other standard manufacturing procedures are described in *Modern Plastics Encyclopedia*, Vol. 46, pp. 62–70 (1969); and in *Pharmaceutical Sciences*, Remington, 14th Ed., pp. 1626–1678 (1970) Mack Publishing Co. Easton, Pa.

Exemplary solvents suitable for manufacturing the wall, a single layer and a bilayer include inert inorganic and organic solvents. The solvents include members selected from the group consisting of aqueous solvents, alcohols, ketones, esters, ethers, aliphatic hydrocarbons, halogenated solvents, cycloaliphatics, aromatics, heterocyclic solvents and mixtures thereof. Typical solvents include acetone, diacetone, alcohol, methanol, ethanol, isopropyl alcohol, butyl alcohol, methyl acetate, ethyl acetate, isopropyl acetate, n-butyl acetate, methyl isobutyl ketone, methyl propyl ketone, n-hexane, n-heptane, ethylene glycol monoethyl ether, ethylene glycol monoethyl acetate, methylene dichloride, ethylene dichloride, propylene dichloride, carbon tetrachloride, chloroform, nitroethane, nitropropane, tetrachloroethane, ethyl ether, isopropyl ether, cyclohexane, cyclooctane, benzene, toluene, naphtha, tetrahydrofuran, diglyme, and aqueous and nonaqueous mixtures thereof, such as acetone and water, acetone and methanol, acetone and ethyl alcohol, methylene dichloride and methanol, and ethylene dichloride and methanol.

DESCRIPTION OF EXAMPLES OF THE INVENTION

The following examples are illustrative of the present invention, and they should not be considered as limiting the scope of the invention in any way, as these examples and other equivalents thereof will become apparent to those versed in the art in light of the present disclosure, drawings and accompanying claims.

Example 1

A drug phenytoin composition is prepared as follows: first, 2,580 g of polyethylene oxide having a weight-average molecular weight of 200,000 is passed through a 40-mesh screen. Then, 1,290 g of the screened polyethylene oxide is placed into the bowl of a mixer. Then, 2,400 g of sodium phenytoin is placed in the bowl over the polyethylene oxide. Next, 300 g of polyvinylpyrrolidone of 40,000 viscosity-average molecular weight is passed through a 40-mesh screen and added to the mixer. The remaining 1,290 g of polyethylene oxide is then added to the bowl. Next, 300 g of sorbitol and 360 g of tromethamine USP (2-amino-2-hydroxymethyl-1,3-propanediol) is passed through a 40-mesh screen and added to the mixer. The addition of the dry ingredients into the bowl is performed with the sodium phenytoin located between the two layers of polyethylene oxide. The ingredients are mixed for 5 minutes to produce a homogenous blend. The granulation process is initiated by the gradual addition of 3,200 g of ethyl alcohol to the mixer with continuous mixing. Mixing is continued over a period of 5 to 10 minutes to effect a consistency to change the dry powder to granules. The wet granulation is dried at 40° C. for 16 hours and then passed through a fluid air mill with a 7-mesh screen for size reduction. Next, the size reduced granules are placed into a blender. Then, 60 g of magnesium stearate that has been passed through a 60-mesh screen is added to the granulation, and all the ingredients mixed for a minute. This preparation provides a phenytoin composition comprising sodium phenytoin, polyethylene oxide, polyvinylpyrrolidone, tromethamine, sorbitol and magnesium stearate, useful for the therapeutic management of epilepsies.

Example 2

A composition possessing expandable kinetics is prepared as follows: first, a binder solution is prepared by adding 300 g of polyvinylpyrrolidone of 40,000 average-molecular weight to a mixer containing 2,700 g of water. Then, the mixture is stirred until the polyvinylpyrrolidone dissolves in the water and forms a clear binder solution.

Next, granules for forming an expandable, osmotic composition are prepared as follows: first, 7,370 g of polyethylene oxide having an average-molecular weight of 7,000,000 is placed into the bowl of a fluid bed granulator. Then, 200 g of polyvinylpyrrolidone possessing an average-molecular weight of 40,000 is added to the granulator. Next, 2,000 g of sodium chloride and 100 g of red ferric oxide, which was milled using a 21-mesh screen are added to the granulator. The powder ingredients are fluidized for 3 minutes to produce a uniform mixing of the powders. Next, the binder solution is sprayed onto the powders at a solution spray rate of 50 g/min. During the spraying process the process air flow is maintained at 500 cfm and the temperature maintained at 24° C. During the spraying operation the solution is sprayed for 30 seconds, followed by a shaking time of 10 seconds. At the end of the spraying operation, the granules are dried in the granulator for an additional 10 to 15 minutes to obtain a dry granulation. The granules are passed through a fluid air mill with a 7-mesh screen for size reduction. The size reduced granules then are placed into a blender. Then, 25 g of magnesium stearate, previously screened through a 40-mesh screen, and 5 g of powdered butylated hydroxytoluene, previously screened through a 60-mesh screen, are added to the granules and mixed together to provide an osmotically expandable composition.

Example 3

A bilayer core is manufactured by compressing in layered arrangement the sodium phenytoin composition and the osmotic expandable composition described above as follows: first, 750 mg of the sodium phenytoin composition is added into the cavity of a 5/16-in. (8-mm) diameter, and then 300 mg of the osmotic expandable composition is placed into the die and the two compositions compressed into layered arrangement with 1 ton (2,000 lb.) of pressure.

The bilayered core just described is coated with a subcoat comprising 70% hydroxypropylcellulose possessing a 80,000 average molecular weight and 30% of hydroxypropylmethylcellulose possessing a 9,600 average molecular weight. The composition is dissolved in distilled water to produce a solid composition of the solution of 6%. The compressed cores are placed into a 12-in. (30-cm) coating pan and the coating solution is sprayed onto the bilayer compressed cores at a spray rate of 8 g/min in order to obtain a subcoat weight of 45 mg. The spray-subcoat temperature is 40° C. to effect the coating of the bilayer cores.

Next, a wall forming composition comprising 90% cellulose acetate having an acetyl content of 32% and 10% polyethylene glycol having a molecular weight of 3,350 is dissolved in a solvent. The solvent comprises acetone and water, 88:12, wt:wt, to effect a solid composition of the solution of 5%. Then, the subcoated bilayer cores are placed into a 12-inch (30-cm) coating pan and the coating solution is sprayed onto the subcoated-bilayer cores at a spray rate of 25 g/min. The coating temperature is 35° C. to apply 140 mg of the semipermeable wall around and in contact with the subcoat.

Next, a 50-mil (1.27 mm) passageway is drilled through the semipermeable wall and subcoat into the sodium phenytoin side of the dosage form. The residual solvent is removed by drying at 45° C. and 45% relative humidity in an oven for 48 hours. At the end of the drying, the humidity is turned off and the dosage forms are dried at 45° C. for an additional 4 hours, to provide an osmotic dosage form for orally administering phenytoin to a patient suffering with the symptoms of epilepsy.

Example 4

A dosage form is manufactured according to the above examples to provide a dosage form for oral administration. The dosage form comprises a drug phenytoin composition comprising 40% sodium phenytoin, 43% polyethylene oxide having an average-molecular weight of 200,000, 5% sorbitol, 6% tromethamine, 5% polyvinylpyrrolidone and 1% magnesium stearate; and an expandable composition comprising 73.7% polyethylene oxide of 7,000,000 average-molecular weight, 20% osmagent sodium chloride, 5% polyvinylpyrrolidone of 40.000 molecular weight, 1% red ferric oxide, 0.25% magnesium stearate and 0.05% butylated hydroxytoluene. The subcoat comprises 70% hydroxypropylcellulose of 80,000 molecular weight and 30% hydroxypropylmethylcellulose of 11,300 molecular weight. The semipermeable wall comprises 90% cellulose acetate having a 32% acetyl content and 10% polyethylene glycol of 3,350 molecular weight. The dosage form comprises a 1.27 mm passageway and releases the phenytoin at an average rate of 30 mg/hr. The dosage form released the phenytoin at the following rate in mg/hr over time: 0.46 in the first hour, 9.99 in the second hour, 18.04 in the third hour, 29.19 in the fourth hour, 28.71 in the fifth hour, 30.85 in the sixth hour, 31.78 in the seventh hour, 30.43 in the eighth hour, 30.73 in the ninth hour, 29.15 in the tenth hour, 18.81 in the eleventh hour, and 6.55 in the twelfth hour. The dosage form provided by the example exhibits an average release rate of 0.46 mg/hr to 30 mg/hr over a 12 hour period.

Example 5

A dosage form for the controlled delivery of phenytoin is manufactured according to the following example: First, 2,580 g of polyethylene oxide having an average-molecular weight of 200,000 is passed through a 40-mesh screen. Next, 1,290 g of the screened polyethylene oxide is placed into a Hobart mixer. Then, 2,400 g of sodium phenytoin is placed in the mixer over the polyethylene oxide. Next, 300 g of polyvinylpyrrolidone of 40,000 molecular weight is passed through a 40-mesh screen and added to the mixer. The remaining 1,290 g of polyethylene oxide is then added to the mixer. Next, 300 g of sorbitol and 360 g of tromethamine USP, which are passed through a 40-mesh screen, are added to the mixer. The addition of ingredients into the mixer is performed so the sodium phenytoin is located in between the two layers of polyethylene oxide. The powders are mixed for 5 minutes until a homogenous blend is produced. The granulation process is initiated by the gradual addition of 3,200 g of ethyl alcohol to the mixer with continued mixing. Mixing is continued over a period of 5 to 10 minutes such that the consistency of the dry powder changes to granules. The wet granulation is dried at 40° C. for 16 hours and then passed through a fluid air mill with a 7-mesh screen for size reduction. The size reduced granules are placed into a blender. Next, 60 g of magnesium stearate which has been passed through a 60-mesh screen is added to the granulation and all the ingredients are mixed for an additional 1 minute.

Next, a composition for pushing the sodium phenytoin from the dosage form is prepared as follows: first, 300 g of polyvinylpyrrolidone having an average-molecular weight of 40,000 is added to a mixer containing 2,700 g of water. This mixture is stirred until the, polyvinylpyrrolidone dissolves in water and a clear solution is formed. This solution is referred to as the binder solution.

Next, 6,370 g of polyethylene oxide having an average-molecular weight of 2,000,000 is placed into the bowl of a fluid bed granulator. Next, 200 of polyvinylpyrrolidone having an average-molecular weight of 40,000 is added to the bowl. Then, 3,000 g of sodium chloride and 100 g of red ferric oxide which have been milled using a 21-mesh screen is then placed into the bowl. The bowl is attached to the main body of the granulator and the granulation process is then initiated and fluidized for 3 minute to obtain uniform mixing of the powders. Next, the binder solution is sprayed onto the powder bed through nozzles at a rate of 50 g/min. During the spraying process, the process air flow is maintained at 500 cfm and the product temperature is maintained at 24° C. During the spraying operation, the solution is sprayed for 30 seconds followed by a shaking time of 10 seconds. At the end of the spraying operation, the granules are dried in the granulating chamber for an additional 10 to 15 minutes to obtain dry granulation. The granules are then passed through a fluid air mill with a 7-mesh screen for size reduction. The size-reduced granules then are placed into a blender. Next, 25 g of magnesium stearate screened through a 40-mesh screen and 5 g of powdered butylated hydroxytoluene screened through a 60-mesh screen are added to the granules and mixed together.

The sodium phenytoin composition and the osmotic composition are compressed together. First, 750 mg of sodium phenytoin granules is added into the cavity of a 5/16 in. diameter die, tamped, and then 300 mg of the osmotic granules is placed into the die and compressed together using 1 ton of pressure.

Next, a subcoat composed of 70% hydroxypropylcellulose and 30% of hydroxypropylmethylcellulose is dissolved in water to produce a solution with solids composition of 6%. The compressed layers are placed into a 12-in. coating pan and the coating solution is sprayed onto the layers at a rate of 8 g/min/gun. The temperature is maintained at 40° C., and the coating process is continued until 58 mg amount of subcoat composition has been sprayed onto the compressed layers.

The semipermeable wall is composed of 90% cellulose acetate having an acetyl content of 32.0% and 10% polyethylene glycol having an average-molecular weight of 3,350. The semipermeable wall composition is dissolved in a mixture of acetone and water (the solvents are mixed together in a ratio of 88:12 wt:wt) with a solid composition of 5%. The subcoated bilayer cores are placed into a 12-in. coating pan and the coating solution is sprayed onto the bilayer cores at a rate of 25 g/min/gun. The temperature is maintained at 35° C., the coating process is continued until 125 mg of semipermeable composition has been sprayed onto the subcoated bilayer cores.

Next, one 50-mil orifice is drilled on the drug layer side of the dosage forms. The residual solvents remaining after the coating are removed by drying the systems at 45° C. and 45% relative humidity in an oven for 48 hours. At the end of this drying the humidity is turned off and the systems are dried at 45° C. for an additional 4 hours.

The dosage form manufactured as described above comprises 300 mg sodium phenytoin, 322.5 mg polyethylene oxide of average-molecular weight 200,000, 37.5 mg sorbitol, 45 mg tromethamine, 37.5 mg polyvinylpyrrolidone and 7.5 mg magnesium stearate in the first layer. The second layer contains 191.1 mg polyethylene oxide of average-molecular weight 2,000,000, 90 mg sodium chloride, 15 mg polyvinylpyrrolidone, 3 mg red ferric oxide, 0.75 mg magnesium stearate and 0.15 mg butylated hydroxytoluene. The subcoat is composed of 40.6 mg hydroxypropylcellulose and 17.4 mg hydroxypropylmethylcellulose. The semipermeable wall comprises 112.5 mg cellulose acetate of average acetyl content 32.0% and 12.5 mg polyethylene glycol of average-molecular weight 3,350. The dosage delivers sodium phenytoin at an average rate of 30 mg/hr for 12 hours. The release rate pattern for the dosage form in mg/hr over hrs is as follows: 0.62 in first hour, 11.57 in second hour, 22.37 in third hour, 27.67 in fourth hour, 30.5 in fifth hour, 32.7 in sixth hour, 32.7 in seventh hour, 32.9 in eighth hour, 30.6 in ninth hour, 30.7 in tenth hour, 15.19 in eleventh hour, and 4.86 in twelfth hour.

Example 6

An osmotic dosage form designed and shaped for oral administration to a patient in need of phenytoin therapy is manufactured by following the above examples. In this manufacture the composition comprising phenytoin is prepared as in Example 5. The binder solution used in this example is made as follows: first, 300 g of polyvinylpyrrolidone having a molecular weight of 40,000 is added to a mixing vessel containing 2,700 g of water. This mixture is stirred until the polyvinylpyrrolidone dissolves in water and a clear solution is formed.

Next, 7,375 g of sodium carboxymethylcellulose having an average molecular weight of 700,000 is placed into the bowl of a fluid bed granulator. Next, 200 g of polyvinylpyrrolidone having an average-molecular weight of 40,000 is added to the bowl. 2,000 g of sodium chloride and 100 g of red ferric oxide which have been milled using a 21-mesh screen are then placed into the bowl. The bowl is attached to the main body of the granulator and the granulation process is initiated. Initially, the powder bed inside the bowl is fluidized for 3 minute to obtain uniform mixing of the powders. Next, the binder solution is sprayed onto the powder bed through nozzles at a rate of 50 g/min. During the spraying process the process air flow is maintained at 500 cfm and the product temperature is maintained at 24° C. The solution is sprayed for 30 seconds, followed by a shaking time of 10 seconds. At the end of the spraying operation the granules are dried in the granulating chamber for 10 to 15 minutes to obtain dry granulation. The granules are passed through a fluid air mill with a 7-mesh screen for size reduction. Next, the size-reduced granules are then placed into a blender. Then, 25 g of magnesium stearate screened through a 40-mesh screen is added to the granules and they are mixed together.

The sodium phenytoin drug composition identified as (layer 1), and the osmotic granules identified as (layer 2), are compressed together to form a bilayer tablet. First, 750 mg of sodium phenytoin granules (layer 1), is added into the cavity of a 5/16-in. diameter die, tamped, and then 300 mg of the osmotic composite granulation identified as (layer 2), is placed into the die and compressed together using 1 ton of pressure to provide the intended bilayer compressed tablet.

Next, the bilayer compressed tablet is coated with an interior coat, also identified as a subcoat. The coating composition comprises 70% hydroxypropylcellulose and 30% of hydroxypropylmethylcellulose. The subcoat composition is dissolved in water to produce a solid composition of 6%. The compressed bilayers are placed into a 12-in. coating pan and the coating solution is sprayed onto the bilayer tablets at a rate of 8 g/min/gun. The product temperature is maintained at 40° C. The coating process is stopped when 58 mg of subcoat composition has been sprayed onto the compressed bilayer tablets.

Next, a semipermeable wall, identified as an exterior overcoat, comprising 97% cellulose acetate having an acetyl content of 32% and 3% polyethylene glycol having a molecular weight of 3,350 is coated over and in contact with the outer surface of the interior wall or subcoat. The semipermeable wall-forming composition is dissolved in a mixture of acetone and water (the solvents are mixed together in a ratio of 90:10 wt:wt) such that the solids composition of the solution is 5%. The subcoated bilayered tablets are placed into a 12-in. coating pan and the coating solution is sprayed onto the subcoated bilayer tablets at a rate of 25 g/min/gun. The product temperature is maintained at 35° C., the coating process is stopped when 140 mg of semipermeable membrane composition has been sprayed onto the compressed systems.

Next, one 50-mil orifice is drilled on the drug-layer side of the dosage forms. The residual solvents remaining after the coating are removed by drying the systems at 45° C. and 45% relative humidity in an oven for 48 hours. At the end of this drying cycle, the humidity is turned off and the dosage forms are dried at 45° C. for an additional 4 hours to complete the drying process.

Example 7

The present invention provides for the release-rate of phenytoin over time with a different rate of release. The rates of release are obtained by changing, in one manufacture, the composition of the wall. For example, a slow to fast rate of release, wherein the rate of release is 5 mg/hr to 60 mg/hr, is effected by increasing the concentration of flux enhancer, for example polyethylene glycol of 400 to 600 average molecular weight in the wall to 1% to 20%.

Example 8

First, a binder solution is prepared as follows: 200 g of polyvinyl pyrrolidone having an average molecular weight of 40,000 is added to a mixing vessel containing 2000 g of water. This mixture is stirred until the plyvinylpyrrolidone dissolves in water and a clear solution is formed. Then, a composition comprising phenytoin granules is prepared as follows: first, 3356 g of polyethylene oxide having an average molecular weight of 200,000 is placed into the bowl of a fluid bed granulator. Next, 3200 g phenytoin and 200 g of polyvinylpyrrolidone is placed in the bowl of the fluid bed granulator. Next 400 g of sorbitol and 480 g of tromethamine, are placed into the bowl. The bowl is attached to the main body of the granulator and the granulation process is then initiated. Initially, the powder bed inside the bowl is fluidized for 2 minutes to obtain uniform mixing of the powders. Next, the binder solution is sprayed onto the powder bed through nozzles at a rate of 50 g/min/gun. During the spraying process, the process air flow is adjusted to maintain bed fluidization and the product temperature is maintained at 28° C. During the spraying operation, the solution is sprayed for 30 seconds followed by a shaking time of 10 seconds during which time the powders adhering to the filterbags may be dislodged into the granulating chamber. At the end of the spraying operation, the granules are dried in the granulating chamber for an additional 15 to 30 minutes to obtain dry granulation. The process parameters may be adjusted to obtain a quality product. The granules are then passed through a fluid air mill with a 7 mesh screen for size reduction. The size reduced granules are then placed into a suitable blender. 80 g of magnesium stearate (screened through a 40 mesh) and 4 g of powdered butylated hydroxy toluene (screened through a 60 mesh) and 80 g of sodium lauryl sulfate (screened through a 40 mesh screen) is added to the granules and mixed together.

Next, a second binder solution is prepared as follows: first, 300 g of polyvinyl pyrrolidone having an average molecular weight of 40,000 is added to a mixing vessel containing 2700 g of water. This mixture is stirred until the polyvinyl pyrrolidone dissolves in water and a clear solution is formed.

Next, 7370 g of polyethylene oxide having an average molecular weight of 7,000,000 is placed into the bowl of a fluid bed granulator. Next, 200 g of polyvinyl pyrrolidone having an average molecular weight of 40,000 is added to the bowl. 2000 g of sodium chloride and 100 g of red ferric oxide which have been milled using a 21 mesh screen is then placed into the bowl. The bowl is attached to the main body of the granulator and the granulation process is then initiated. Initially, the powder bed inside the bowl is fluidized for 3 minute to obtain uniform mixing of the powders. Next, the binder solution is sprayed onto the powder bed through nozzles such that the solution is sprayed at a rate of 50 g/min. During the spraying process, the process air flow is maintained at 500 cfm and the product temperature is maintained at 24° C. During the spraying operation, the solution is sprayed for 30 seconds followed by a shaking time of 10 seconds during which time the powders adhering to the filterbags may be dislodged into the granulating chamber. At the end of the spraying operation, the granules are dried in the granulating chamber for an additional 10 to 15 minutes to obtain dry granulation. The process parameters may be adjusted to obtain a quality product. The granules are then passed through a fluid air mill with a 7 mesh screen for size reduction. The size reduced granules are then placed into a suitable blender. 25 g of magnesium stearate (screened through a 40 mesh) and 5 g of powdered butylated hydroxy toluene (screened through a 60 mesh) is added to the granules and mixed together.

Next, sodium phenytoin granules and the osmotic hydrogel-osmagent granules are compressed together. First, 750 mg of sodium phenytoin granules (layer 1, also identified as composition 21) is added into the die cavity of a 5/16" diameter modified ball tooling, tamped, and then 300 mg of the osmotic layer granulation (layer 2, also identified as composition 22) is placed into the die and compressed together using 1 ton of pressure.

Next, a subcoat is prepared as follows: the subcoat is composed of 70% hydroxy propyl cellulose and 30% of hydroxy propyl methyl cellulose. The subcoat composition is dissolved in water to provide a solid composition of the solution is 6%. The compressed systems are placed into a 12" coating pan and the coating solution is sprayed onto the tablets with the solution sprayed at a rate of 8 g/min/gun so that 40 mg of subcoat membrane is applied. The temperature is maintained at 40° C. the coating process is stopped when the subcoat composition has been sprayed onto the compressed systems.

Next, a semipermeable wall, also identified as a semipermeable membrane, is prepared comprising 90% cellulose acetate 320 (having an acetyl content of 32%) and 10% polyethylene glycol having an average molecular weight of 3350. The semipermeable membrane composition is dissolved in a mixture of acetone and water (the solvents are mixed together in a ratio of 88:12 w:wt), Such that solids composition of the solution is 5%. The subcoated bilayer cores are placed into a 12" coating pan and the coating solution is sprayed onto the cores at a rate of 25 g/min/gun. The process temperature is maintained at 35° C., the coating process is stopped when 120 mg of semipermeable membrane composition has been sprayed onto the subcoated cores.

Next, one 50 mil (1.27 mm) orifice is drilled, using a mechanical drill bit or a laser, on the drug layer side of the coated systems. The residual solvents remaining after the coating is removed by drying the systems at 45° C. and 45% relative humidity in an oven for 48 hrs. At the end of this drying cycle, the humidity is turned off and the systems are dried at 45° C. for an additional 4 hours to complete the drying process.

A novel dosage form manufactured as described above, comprises in the first layer 40% sodium phenytoin, 41.95% polyethylene oxide of average molecular weight 200,000, 5% sorbitol, 6% tromethamine, 5% polyvinyl pyrrolidone, 1% sodium lauryl sulfate, 1% magnesium stearate, and 0.05% of butylated hydroxytoluene. The second layer contains 73.7% polyethylene oxide of average molecular weight 7,000,000, 20% sodium chloride, 5% polyvinyl pyrrolidone, 1% red ferric oxide, 0.25% magnesium stearate and 0.05% butylated hydroxy toluene. The subcoat comprises 70% hydroxypropyl cellulose and 30% hydroxypropyl methyl cellulose. The semipermeable membrane exterior coat comprises 90% cellulose acetate of average acetyl content 32% and 10% polyethylene glycol of average molecular weight 3350.

The dosage form possessed the following drug release-rate pattern for delivering phenytoin orally to a patient: 1.85 mg in the first hour, 11.74 mg in the second hour, 17.49 mg in the third hour, 21.37 mg in the fourth hour, 27.32 mg in the fifth hour, 27.15 mg in the sixth hour, 31.34 mg in the seventh hour, 31.10 mg in the eighth hour, 29.0 mg in the ninth hour, 27.17 mg in the tenth hour, 20.06 mg in the eleventh hour and 7.06 mg in the twelfth hour.

Example 9

A dosage form, designed, shaped, and adapted for delivering phenytoin to a patient orally is manufactured as follows: first, 3555 g of polyethylene oxide having an average molecular weight of 200,000 is passed through a 40 mesh screen. 1777.5 g of the screened polyethylene oxide is placed into the bowl of a mixer. 1500 g of sodium phenytoin is then placed in the bowl over the polethylene oxide. Next, 300 g of polyvinyl pyrrolidone which is passed through a 40 mesh screen is added to the bowl. The remaining 1,777.5 g of polyethylene oxide is then added to the bowl. Next, 300 g of sorbitol and 225 g of tromethamine, which are passed through a 40 mesh screen is added to the bowl. The addition of dry ingredients into the bowl is performed with the sodium phenytoin located in between the two layers of polyethylene oxide. The powder is mixed for 5 minutes until a homogeneous blend is produced. The granulation process is initiated by the gradual addition of 3200 g of ethyl alcohol to the mixer with continued mixing. Mixing is continued over a period of 5 to 10 minutes so the consistency of the dry powder changes to that of granules. The wet granulation is dried at 40° C. for 16 hours and then passed through a fluid air mill with a 7 mesh screen for size reduction. The size reduced granules are then placed into a blender. Next, 60 g of magnesium stearate and 60 g of sodium lauryl sulfate which has been passed through a 60 mesh is added to the granulation and all the ingredients are mixed for an additional 1 minute.

Next, 300 g of polyvinyl pyrrolidone having an average molecular weight of 40,000 is added to a mixing vessel containing 2700 g of water. This mixture is stirred until the PVP K29-32 dissolves in water and a clear solution is formed. This solution is referred to as a binder solution.

Then, 7370 g of polyethylene oxide having an average molecular weight of 7,000,000 is placed into the bowl of a fluid bed granulator. Next, 200 g of polyvinyl pyrrolidone having an average molecular weight of 40,000 is added to the bowl. 2000 g of sodium chloride and 100 g of red ferric oxide which have been milled using a 21 mesh screen is then placed into the bowl. The bowl is attached to the main body of the granulator and the granulation process is initiated. Initially, the powder bed inside the bowl is fluidized for 3 minutes to obtain uniform mixing of the powders. Next, the binder solution is sprayed onto the powder bed through nozzles at a rate of 50 g/min. During the spraying process, the process air flow is maintained at 500 cfm and the product temperature is maintained at 24° C. During the spraying operation, the solution is sprayed for 30 seconds followed by a shaking time of 10 seconds during which time the powders adhering to the filterbags may be dislodged into the granulating chamber. At the end of the spraying operation, the granules are dried in the granulating chamber for an additional 10 to 15 minutes to obtain dry granulation. The granules are passed through a fluid air mill with a 7 mesh screen for size reduction. The size reduced granules are then placed into a blender. 25 g of magnesium stearate (screened through a 40 mesh) and 5 g of powdered butylated hydroxy toluene (screened through a 60 mesh) is added to the granules and mixed together.

The drug sodium phenytoin granules and the osmogel-osmoagent granules are compressed together. First, 400 mg of sodium phenytoin granules (layer 1) is added into the cavity of a ¼" diameter die, tamped, and then 160 mg of the osmotic layer granulation (layer 2) is placed into the die and compressed together using 1 ton of pressure.

Next, a subcoat is prepared comprising 70% hydroxy propyl cellulose and 30% of hydroxy propyl methyl cellulose. The subcoat composition is dissolved in water, to provide solids composition of 6%. The compressed layers are placed into a 12" coating pan and the coating solution is sprayed onto the layers at a rate of 8 g/min/gun. The process temperature is maintained at 40° C., the coating process is stopped when the subcoat composition has been sprayed onto the compressed layers.

Next, a semipermeable wall is prepared comprising 97% cellulose acetate (having an acetyl content of 32.0) and 3% polyethylene glycol having an average molecular weight of 3350. The semipermeable composition is dissolved in a mixture of acetone and water (the solvents are mixed together in a ratio of 88:12 w:wt), with a solid composition of 5%. The subcoated layers are placed into a 12" coating pan and the coating solution is sprayed onto the layers at a rate of 25 g/min/gun. The process temperature is maintained at 35° C., the coating process is stopped when the semipermeable composition has been sprayed onto the subcoated systems.

Next one 30 mil (0.762 mm) orifice is drilled, on the drug layer side of the coated layers. The residual solvents remaining after the coating is removed by drying at 45° C. and 45% relative humidity in an oven for 48 hrs. At the end of this drying cycle, the humidity is turned off and the coated layers are dried at 45° C. for an additional 4 hours to complete the drying process.

The dosage form manufactured as described above comprises 25% sodium phenytoin, 59.25% polyethylene oxide of average molecular weight 200,000, 5% sorbitol, 3.75% tromethamine, 5% polyvinyl pyrrolidone, 1% magnesium stearate and 1% sodium lauryl sulfate in the first layer. The second push layer comprises 73.7% polyethylene oxide of average molecular weight 7,000,000, 20% sodium chloride, 5% polyvinyl pyrrolidone, 1% red ferric oxide, 0.25% magnesium stearate and 0.05% butylated hydroxy toluene.

The subcoat comprises 70% hydroxypropyl cellulose and 30% hydroxypropyl methyl cellulose. The semipermeable exterior coat comprises 97% cellulose acetate of average acetyl content 32% and 3% polyethylene glycol of average molecular weight 3350. The dosage form delivers sodium phenytoin at the average rate of 10 mg/hr.

The drug release pattern for the dosage form manufactured by the example delivers sodium phenytoin as follows: 1.31 mg in the first hour, 8.33 mg in the second hour, 10.03 mg in the third hour, 9.87 mg in the fourth hour, 11.03 mg in the fifth hour, 11.32 mg in the sixth hour, 11.02 mg in the seventh hour, 10.91 mg in the eighth hour, 8.55 mg in the ninth hour, 6.6 mg in the tenth hour, 4.0 mg in the eleventh hour and 1.77 mg in the twelfth hour.

Example 10

A dosage form manufactured as an osmotic tablet is prepared as follows: first, 4038 g of polyethylene oxide having an average molecular weight of 200,000 is passed through a 40 mesh screen. Then, 2019 g of the screened polyethylene oxide is placed into the bowl of a mixer. Next, 1080 g of sodium phenytoin is then placed in the bowl over the polyethylene oxide. Next, 300 g of polyvinyl pyrrolidone which is passed through a 40 mesh screen is added to the bowl. The remaining 2019 g of polyethylene oxide is then added to the bowl. Next, 300 g of sorbitol and 162 g of tromethamine, USP which are passed through a 40 mesh screen is added to the bowl. The addition of dry ingredients into the bowl is performed with the sodium phenytoin located between the two layers of polyethylene oxide. The powder is mixed for 5 minutes until a homogeneous blend is produced. The granulation process is initiated by the gradual addition of 3200 g of ethyl alcohol to the mixer with continued mixing. Mixing is continued over a period of 5 to 10 minutes, the dry powder changes to granules. The wet granulation is dried at 40° C. for 16 hours and then passed through a fluid air mill with a 7 mesh screen for size reduction. The size reduced granules are then placed into a blender. Next, 60 g of magnesium stearate and 60 g of sodium lauryl sulfate which has been passed through a 60 mesh is added to the granulation and all the ingredients are mixed for an additional 1 minute.

A binder solution is prepared as follows: first, 300 g of polyvinyl pyrrolidone having an average molecular weight of 40,000 is added to a mixing vessel containing 2700 g of water. This mixture is stirred until the PVP K29-32 dissolves in water and a clear solution is formed, to produce the binder solution.

Next, a displacement or push composition is prepared as follows: first, 7370 g of polyethylene oxide having an average molecular weight of 7,000,000 is placed into the bowl of a fluid bed granulator. Next, 200 g of polyvinyl pyrrolidone having an average molecular weight of 40,000 is added to the bowl. Then 2000 g of sodium chloride and 100 g of red ferric oxide which have been milled using a 21 mesh screen is placed into the bowl. The bowl is attached to the main body of the granulator and the granulation process is then initiated. Initially, the powder bed inside the bowl is fluidized for 3 minute to obtain uniform mixing of the powders. Next, the binder solution is sprayed onto the powder bed through nozzles at a rate of 50 g/min. During the spraying process, the process air flow is maintained at 500 cfm and the product temperature is maintained at 24° C. During the spraying operation, the solution is sprayed for 30 seconds followed by a shaking time of 10 seconds during which time all the powders are deposited into the granulating chamber. At the end of the spraying operation, the granules are dried in the granulating chamber for an additional 10 to 15 minutes to obtain dry granulation. The granules are then passed through a fluid air mill with a 7 mesh screen for size reduction. The size reduced granules are then placed into a blender. Next, 25 g of magnesium stearate (screened through a 40 mesh) and 5 g of powdered butylated hydroxy toluene (BHT) (screened through a 60 mesh) is added to the granules and mixed together.

Next, the sodium phenytoin granules and the osmotic displacement granules are compressed together. First, 556 mg of sodium phenytoin granules (layer 1) is added into the die cavity of a ⁵⁄₃₂" diameter, tamped, and then 222 mg of the osmotic layer granulation (layer 2) is placed into the die and compressed together using 1 ton of pressure.

Next, a subcoat comprising 70% hydroxyl propyl cellulose and 30% of hydroxy propyl methyl cellulose is dissolved in water, to produce a solids composition of the solution is 6%. The compressed layers are placed into a 12" coating pan and the coating solution is sprayed onto the layers at a rate of 8 g/min/gun. The process temperature is maintained at 40° C., the coating process is stopped when the subcoat composition (33 mg) has been sprayed onto the compressed layers.

Next, a semipermeable membrane comprising of 97% cellulose acetate 320 (having an acetyl content of 32.0) and 3% polyethylene glycol having an average molecular weight of 3350 is dissolved in a mixture of acetone and water (the solvents are mixed together in a ratio of 90:10 wt:wt), with solids composition of the solution is 5%. The subcoated layers are placed into a 12" coating pan and the coating solution is sprayed at a rate of 25 g/min/gun. The product temperature is maintained at 35° C., the coating process is stopped when 120 mg semipermeable membrane composition has been sprayed onto the subcoated layer.

Next, one 30 mil (0.762 mm) orifice is drilled, on the drug layer side of the coated systems. The residual solvents remaining after the coating is removed by drying at 45° C. and 45% relative humidity in an oven for 48 hrs. At the end of this drying cycle, the humidity is turned off and the dosage forms are dried at 45" C. for an additional 4 hours to complete the drying process.

A dosage form manufactured by this example comprises 18% sodium phenytoin, 67.3% polyethylene oxide of average molecular weight 200,000, 5% sorbitol, 2.7% tromethamine, 5% polyvinyl pyrrolidone, 1% sodium lauryl sulfate and 1% magnesium stearate in the first layer. The second layer comprises 73.7% polyethylene oxide of average molecular weight 7,000,000, 20% sodium chloride, 5% polyvinyl pyrrolidone,1% red ferric oxide, 0.25% magnesium stearate and 0.05% butylated hydroxy toluene. The subcoat comprises 70% hydroxypropyl cellulose and 30% hydroxypropyl methyl cellulose. The semipermeable membrane coat comprises 97% cellulose acetate of average acetyl content 32.0% and 3% polyethylene glycol of average molecular weight 3350.

The dosage form exhibited the following release rate profile for delivering phenytoin: 1.51 mg in the first hour, 8.33 mg in the second hour, 10.41 in the third hour, 11.06 mg in the fourth hour, 10.79 mg in the fifth hour, 10.83 mg in the sixth hour, 10.68 mg in the seventh hour, 10.37 mg in the eighth hour, 9.81 mg in the ninth hour, 8.09 mg in the tenth hour, 5.40 mg in the eleventh hour and 3.65 mg in the twelfth hour.

Example 11

A dosage form for delivering 30 mg of phenytoin to a patient orally is prepared as follows: first, 4,167 g of polyethylene oxide having an average molecular weight of 200,000 is passed through a 40 mesh screen. Then, 2083.5 g of the screened polyethylene oxide is placed into the bowl of a mixer. Next, 1020 g of sodium phenytoin is then placed in the bowl over the polyethylene oxide. Next, 300 g of polyvinylpyrrolidone which is passed through a 40 mesh screen is added to the bowl. The remaining 2,083.5 g of polyethylene oxide is then added to the bowl. Next, 300 g of sorbitol and 153 g of tromethamine, USP which are passed through a 40 mesh screen is added to the bowl. The powder is mixed for 5 minutes until a homogeneous blend is produced. The granulation process is initiated by the gradual addition of 3200 g of ethyl alcohol to the mixer with continued mixing. Mixing is continued over a period of 5 to 10 minutes. The wet granulation is dried at 40° C. for 16 hours and then passed through a fluid air mill with a 7 mesh screen for size reduction. The size reduced granules are then placed into a suitable blender. Next, 60 g of magnesium stearate which has been passed through a 60 mesh is added to the granulation and all the ingredients are mixed for an additional 1 minute.

Next, a binder solution is prepared as follows: first, 300 g of polyvinyl pyrrolidone having an average molecular weight of 40,000 is added to a mixing vessel containing 2700 g of water. This mixture is stirred until the PVP dissolves in water and a clear solution is formed, to yield the binder solution.

Next, a displacement composition comprising osmotic granules is prepared as follows: first, 7370 g of polyethylene oxide having an average molecular weight of 7,000,000 is placed into the bowl of a fluid bed granulator. Next, 200 g of polyvinyl pyrrolidone (PVP) having an average molecular weight of 40,000 is added to the bowl. Then, 2000 g of sodium chloride and 100 g of red ferric oxide which have been milled using a 21 mesh screen is then placed into the bowl. The bowl is attached to the main body of the granulator and the granulation process is then initiated. Initially, the powder bed inside the bowl is fluidized for 3 minute to obtain uniform mixing of the powders. Next, the binder solution is sprayed onto the powder at a rate of 50 g/min. During the spraying process, the process air flow is maintained at 500 cfm and the product temperature is maintained at 24° C. During the spraying operation, the solution is sprayed for 30 seconds followed by a shaking time of 10 seconds. At the end of the spraying operation, the granules are dried in the granulating chamber for an additional 10 to 15 minutes to obtain dry granulation. The granules are then passed through a fluid air mill with a 7 mesh screen for size reduction. The size reduced granules are then placed into a suitable blender. Next, 25 g of magnesium stearate (screened through a 40 mesh) and 5 g of powdered butylated hydroxy toluene (BHT) (screened through a 60 mesh) is added to the granules and mixed together. Next, the sodium phenytoin granules and the osmotic granules are compressed together. First, 176.5 mg of sodium phenytoin granules (layer 1) is added into the die cavity of a ³⁄₁₆" diameter, tamped, and then 70 mg of the osmotic layer granulation (layer 2) is placed into the die and compressed together using 1 ton of pressure. Next, a subcoat comprising 70% hydroxy propyl cellulose and 30% of hydroxy propyl methyl cellulose is dissolved in water, to yield solids composition of 6%. The compressed layers are placed into a 12" coating pan and the coating solution is sprayed onto the layers such at a rate of 8 g/min/gun. The product temperature is maintained at 40° C., the coating process is stopped when subcoat composition (12 mg) has been sprayed onto the compressed layers.

Next, a semipermeable membrane comprising 90% cellulose acetate (having an acetyl content of 39.8%) and 10% polyethylene glycol having an average molecular weight of 3350 is dissolved in a mixture of acetone and water (the solvents are mixed together in a ratio of 95:5 wt: wt), where the solids in the solution is 5%. The subcoated layers are placed into a 12" coating pan and the coating solution is sprayed at a rate of 25 g/min/gun. The product temperature is maintained at 35° C., the coating process is stopped when semipermeable membrane composition has been sprayed onto the subcoated layers.

Next, one 30 mil (0.762 mm) orifice is drilled, on the drug layer side of the dosage form. The residual solvents remaining after the coating is removed by drying the systems at 45° C. and 45% relative humidity in an oven for 48 hrs. At the end of this drying cycle, the humidity is turned off and the systems are dried at 45° C. for an additional 4 hours to complete the drying process.

The dosage form manufactured as described above is comprised of 17% sodium phenytoin, 69.45% polyethylene oxide of average molecular weight 200,000, 5% sorbitol, 2.55% tromethamine, 5% polyvinyl pyrrolidone, 1% magnesium stearate in the first layer. The second layer comprises 73.7% polyethylene oxide of average molecular weight 7,000,000, 20% sodium chloride, 5% polyvinyl pyrrolidone, 1% red ferric oxide, 0.25% magnesium stearate and 0.05% butylated hydroxy toluene. The subcoat comprises 70% hydroxypropyl cellulose and 30% hydroxypropyl methyl cellulose. The semipermeable membrane comprises 90% cellulose acetate of average acetyl content 39.8% and 10% polyethylene glycol of average molecular weight 3350. The dosage form releases sodium phenytoin at the average rate of 3 mg/hr for up to 10 hrs.

The dosage form exhibited the following release rate pattern for sodium phenytoin: 0.51 mg in the first hour, 2.87 mg in the second hour, 3.26 mg in the third hour, 3.6 mg in the fourth hour, 3.64 mg in the fifth hour, 3.54 mg in the sixth hour, 3.21 mg in the seventh hour, 3.02 mg in the eighth hour, 2.3 mg in the ninth hour, and 1.4 mg in the tenth hour.

Example 12

A dosage form designed, shaped, and adapted for oral administration is made as follows: first, 4038 g of polyethylene oxide having an average molecular weight of 200,000 is passed through a 40 mesh screen then, 2019 g of the screened polyethylene oxide is placed into the bowl of a mixer. Next, 1080 g of sodium phenytoin is then placed in the bowl over the polyethylene oxide. Next, 300 g of polyvinyl pyrrolidone which is passed through a 40 mesh screen is added to the bowl. The remaining 2019 g of polyethylene oxide is then added to the bowl. Next, 300 g of sorbitol and 162 g of tromethamine, USP which are passed through a 40 mesh screen is added to the bowl. The powder is mixed for 5 minutes until a homogeneous blend is produced. The granulation process is initiated by the gradual addition of 200 g of ethyl alcohol to the mixer with continued mixing. Mixing is continued over a period of 5 to 10 minutes. The wet granulation is dried at 40° C. for 16 hours and then passed through a fluid air mill with a 7 mesh screen for size reduction. The size reduced granules are then placed into a blender. Next, 60 g of magnesium stearate and 60 g of sodium lauryl sulfate which has been passed through a 60 mesh is added to the granulation and all the ingredients are mixed for an additional 1 minute.

A binder solution is prepared as follows: first, 300 g of polyvinyl pyrrolidone (PVP) having an average molecular weight of 40,000 is added to a mixing vessel containing 2700 g of water. This mixture is stirred until the PVP dissolves in water and a clear binder solution is formed.

Next, a composition comprising an osmopolymer is made as follows: first, 7370 g of polyethylene oxide osmopolymer having an average molecular weight of 7,000,000 is placed into the bowl of a fluid bed granulator. Next, 200 g of polyvinyl pyrrolidone having an average molecular weight of 40,000 is added to the bowl. Then, 2000 g of sodium chloride and 100 g of red ferric oxide which have been milled using a 21 mesh screen is then placed into the bowl. The bowl is attached to the main body of the granulator and the granulation process is then initiated. Initially, the powder bed inside the bowl is fluidized for 3 minute to obtain uniform mixing of the powders. Next, the binder solution is sprayed onto the powder bed at a rate of 50 g/min. During the spraying process, the process air flow is maintained at 500 cfm and the product temperature is maintained at 24° C. During the spraying operation, the solution is sprayed for 30 seconds followed by a shaking time of 10 seconds. At the end of the spraying operation, the granules are dried in the granulating chamber for an additional 10 to 15 minutes to obtain dry granulation. The granules are then passed through a fluid air mill with a 7 mesh screen for size reduction. The size reduced granules are then placed into a blender. Next, 25 g of magnesium stearate (screened through a 40 mesh) and 5 g of powdered butylated hydroxy toluene (BHT) (screened through a 60 mesh) is added to the granules and mixed together.

Next, the sodium phenytoin granules and the osmotic granules are compressed together. First, 167 mg of sodium phenytoin granules (layer 1) is added into the die cavity of a 3/16" diameter modified ball tooling, tamped, and then 67 mg of the osmotic layer granulation (layer 2) is placed into the die and compressed together using 1 ton of pressure.

Next, a subcoat composition is prepared comprising 70% hydroxy propyl cellulose and 30% of hydroxy propyl methyl cellulose. The subcoat composition is dissolved in water, for a solids composition of 6%. The compressed layers are placed into a 12" coating pan and the coating solution is sprayed at a rate of 8 g/min/gun. The product temperature is maintained at 40° C., the coating process is stopped when the desired amount of subcoat composition (12 mg) has been sprayed onto the compressed layers.

Next, a semipermeable wall (or membrane) is prepared as follows: the semipermeable membrane comprises 90% cellulose acetate 398 (having an acetyl content of 39.8%) and 10% polyethylene glycol having an average molecular weight of 3350, dissolved in a mixture of acetone and water (the solvents are mixed together in a ratio of 75:5 wt: wt), with a solids composition of 5%. The subcoated layers placed into a 12" coating pan and the coating solution is sprayed at a rate of 25 g/min/gun. The product temperature is maintained at 35° C., the coating process is stopped when the semipermeable membrane composition has been sprayed onto the subcoated systems (115 mg).

Next, one 30 mil (0.762 mm) orifice is drilled, on the drug layer side of the dosage forms. The residual solvents remaining after the coating is removed by drying the systems at 45° C. and 45% relative humidity in an oven for 48 hrs. At the end of this drying cycle, the humidity is turned off and the systems are dried at 45° C. for an additional 4 hours to complete the drying process.

The dosage form manufactured as described above comprises 18% sodium phenytoin, 67.3% polyethylene oxide of average molecular weight 200,000, 5% sorbitol, 2.7% tromethamine, 5% polyvinyl pyrrolidone,1% sodium lauryl sulfate and 1% magnesium stearate in the first layer. The second layer comprises 73.7% polyethylene oxide of average molecular weight 7,000,000, 20% sodium chloride, 5% polyvinyl pyrrolidone, 1% red ferric oxide, 0.25% magnesium stearate and 0.05% butylated hydroxy toluene. The subcoat comprises 70% hydroxypropyl cellulose and 30% hydroxypropyl methyl cellulose. The semipermeable wall comprises 90% cellulose acetate of average acetyl content 39.8% and 10% polyethylene glycol of average molecular weight 3350.

The dosage form exhibits the following drug delivery pattern over a fifteen hour extended therapeutic period, whereas sodium phenytoin is delivered at the rate of: 0.15 mg in the first hour, 1.24 mg in the second hour, 2.34 mg in the third hour, 2.74 mg in the fourth hour, 2.81 mg in the fifth hour, 2.76 mg in the sixth hour, 2.87 mg in the seventh hour, 2.62 mg in the eighth hour, 2.34 mg in the ninth hour, 2.07 mg in the tenth hour, 1.83 mg in the eleventh hour, 1.57 mg in the twelfth hour, 1.41 in the thirteenth hour, 1.19 in the fourteenth hour, and 0.96 in the fifteenth hour.

Example 13

An osmotic dosage form designed and shaped to deliver sodium phenytoin is manufactured as follows: first, 2580 g of polyethylene oxide having an average molecular weight of 200,000 is passed through a 40 mesh screen. Then, 1290 g of the screened polyethylene oxide is placed into the bowl of a mixer. Next, 2400 g of sodium phenytoin is then placed in the bowl over the polyethylene oxide. Next, 300 g of polyvinyl pyrrolidone which is passed through a 40 mesh screen is added to the bowl. The remaining 1290 g of polyethylene oxide is then added to the bowl. Next, 300 g of sorbitol and 360 g of tromethamine, USP which are passed through a 40 mesh screen is added to the bowl. The powder is mixed for 5 minutes until a homogeneous blend is produced. The granulation process is initiated by the gradual addition of 3200 g of ethyl alcohol to the mixer with continued mixing. Mixing is continued over a period of 5 to 10 minutes. The wet granulation is dried at 40° C. for 16 hours and then passed through a fluid air mill with a 7 mesh screen for size reduction. The size reduced granules are then placed into a blender. Next, 60 g of magnesium stearate which has been passed through a 60 mesh is added to the granulation and all the ingredients are mixed for an additional 1 minute.

Next, a binder solution is prepared as follows: first, 300 g of polyvinyl pyrrolidone (PVP) having an average molecular weight of 40,000 is added to a mixing vessel containing 2700 g of water. This mixture is stirred until the PVP dissolves in water and a clear binder solution is formed.

Next, an osmotic composition is prepared as follows: first, 7370 g of polyethylene oxide having an average molecular weight of 7,000,000 is placed into the bowl of a fluid bed granulator. Next, 200 g of polyvinyl pyrrolidone (PVP) having an average molecular weight of 40,000 is added to the bowl. Then, 2000 g of sodium chloride and 100 g of red ferric oxide, which have been milled using a 21 mesh screen is then placed into the bowl. The bowl is attached to the main body of the granulator and the granulation process is then initiated. Initially, the powder bed inside the bowl is fluidized for 3 minute to obtain uniform mixing of the powders. Next, the binder solution is sprayed onto the powder at a rate of 50 g/min. During the spraying process, the process air flow is maintained at 500 cfm and the product temperature is maintained at 24° C. During the spraying operation, the solution is sprayed for 30 seconds followed by a shaking time of 10 seconds. At the end of the spraying operation, the granules are dried in the granulating chamber for an additional 10 to 15 minutes to obtain dry granulation. The granules are passed through a fluid air mill with a 7 mesh screen for size reduction. The size reduced granules are placed into a blender. Then, 25 g of magnesium stearate (screened through a 40 mesh) and 5 g of powdered butylated hydroxy toluene (BHT) (screened through a 60 mesh) is added to the granules and mixed together.

Next, the sodium phenytoin granules and the osmotic granules are compressed together. First, 750 mg of sodium phenytoin granules (layer 1) is added into the die cavity of a ⁵⁄₁₆" diameter, tamped, and then 300 mg of the osmotic layer granulation (layer 2) is placed into the die and compressed together using 1 ton of pressure.

Next, the bilayered arrangement is surrounded with a subcoat. The subcoat is permeable to the passage of fluid and it comprises 70% hydroxy propyl cellulose and 30% of hydroxy propyl methyl cellulose. The subcoat composition is dissolved in water for a solids composition of 6%. The compressed layers are placed into a 12" coating pan and the coating solution is sprayed onto the layers at a rate of 8 g/min/gun to apply 40 mg of subcoat. The product temperature is maintained at 40° C.

Next, a semipermeable wall, or semipermeable membrane is coated around the subcoated bilayer arrangements. The semipermeable membrane comprises 97% cellulose acetate (having an acetyl content of 32%) and 3% polyethylene glycol having an average molecular weight of 3350. The semipermeable membrane composition is dissolved in a mixture of acetone and water (the solvents are mixed together in a ratio of 88:12 w: wt), so the solids composition of the solution is 5%. The subcoated bilayers are placed into a 12" coating pan and the coating solution is sprayed onto the bilayers at a rate of 25 g/min/gun. The product temperature is maintained at 35° C., the coating process is stopped when 140 mg of semipermeable membrane composition has been sprayed onto the subcoated bilayers.

Next, one 50 mil (1.27 mm) orifice is drilled, on the drug layer side of the coated dosage forms. The residual solvents remaining after the coating is removed by drying the systems at 45° C. and 45% relative humidity in an oven for 48 hrs. At the end of this drying cycle, the humidity is turned off and the systems are dried at 45° C. for an additional 4 hours to complete the drying process.

A dosage form manufactured by this example comprises 40% sodium phenytoin, 43% polyethylene oxide of average molecular weight 200,000, 5% sorbitol, 6% tromethamine, 5% polyvinyl pyrrolidone and 1% magnesium stearate. The second layer contains 73.7% polyethylene oxide of average molecular weight 7,000,000, 20% sodium chloride, 5% polyvinyl pyrrolidone, 1% red ferric oxide, 0.25% magnesium stearate and 0.05% butylated hydroxy toluene. The subcoat comprises 70% hydroxypropyl cellulose and 30% hydroxypropyl methyl cellulose. The semipermeable membrane comprises 97% cellulose acetate of average acetyl content 32% and 3% polyethylene glycol of average molecular weight 3350.

The dosage form delivers sodium phenytoin at an average rate of 20 mg/hr and releases as follows: 0.08 mg in the first hour, 2.8 mg in the second hour, 9.43 mg in the third hour, 11.13 mg in the fourth hour, 15.26 mg in the fifth hour, 18.23 mg in the sixth hour, 19.39 mg in the seventh hour, 20.18 mg in the eighth hour, 21.41 mg in the ninth hour, 23.06 mg in the tenth hour, 22.19 mg in the eleventh hour, 21.65 mg in the twelfth hour, 19.67 in the thirteenth hour, 17.63 in the fourteenth hour and 15.13 in the fifteenth hour.

Example 14

Figure 7:
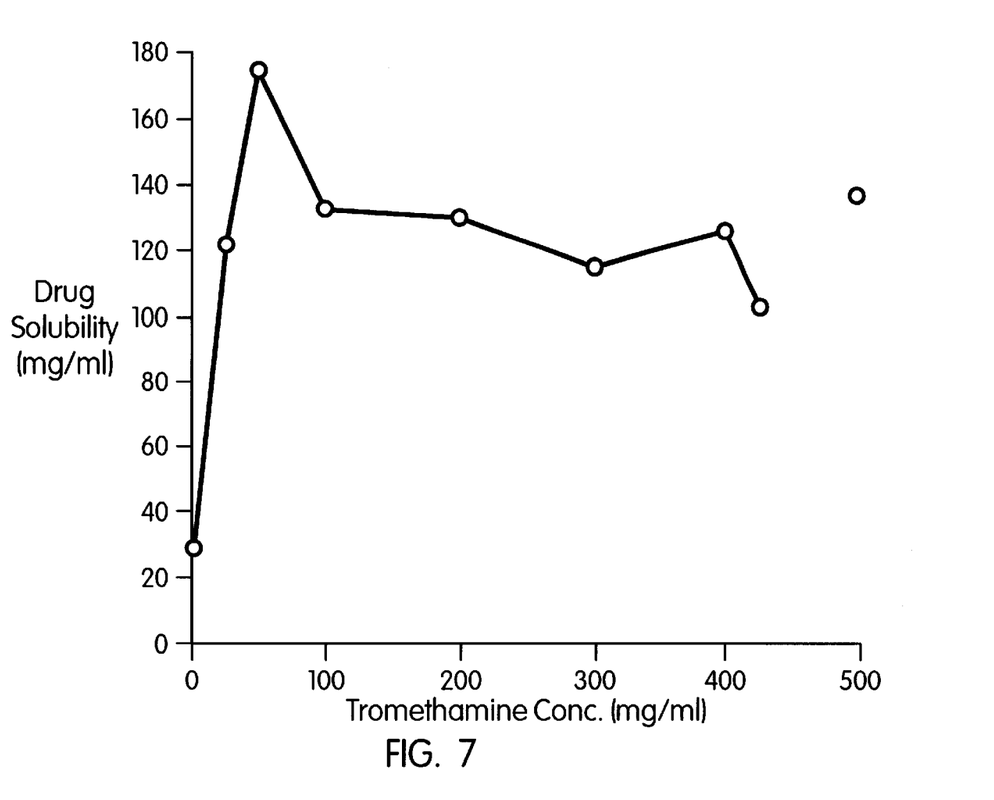
FIG. 7 illustrates an osmotic dosage form comprising sodium phenytoin, and the solubility of sodium phenytoin in tromethamine solutions saturated with the drug.

An osmotic dosage form is manufactured by following the above examples, wherein the dosage form comprises: (a) a drug layer comprising 83 mg to 405 mg of polyethylene oxide, 6 mg to 50 mg of polyvinylpyrrolidone, 3.75 mg to 57 mg of tromethamine, 3 mg to 50 mg of sorbitol, 1.5 mg to 15 mg of magnesium stearate, 0.5 mg to 15 mg of surfactant such as sodium lauryl sulfite and 30 mg to 300 mg of sodium phenytoin; (b) a displacement layer comprising 38 to 280 mg of polyethylene oxide, 9 mg to 120 mg of sodium chloride, 2.25 mg to 20 mg of polyvinylpyrrolidone or 2.25 mg to 20 mg of hydroxypropylmethylcellulose, 0.015 mg to 3 mg of butylated hydroxytoluene; and, 1.5 to 15 mg of magnesium stearate, and 1% of a colorant such as ferric oxide; (c) a coat that surrounds the drug and displacement layers, the coat comprising 6 mg to 45 mg of hydroxypropylcellulose and 2.25 to 18 mg of hydroxypropylmethylcellulose; (d) a wall that surrounds the coat, the wall comprising 60 mg to 140 mg of cellulose acetate comprising a 32% acetyl content, 19 to 32 mg of a cellulose acetate comprising a 39.8 acetyl content, and 6.75 mg to 15 mg of polyethylene glycol; and an exit in the dosage form for delivering the phenytoin to a patient; and (e) the solubility of phenytoin sodium in tromethamine solutions saturated with phenytoin sodium is depicted in FIG. 7, wherein all the tests were performed at 37° C. and the phenytoin sodium solubility was obtained using a U.V. spectrophotometer.

Method of Using the Invention for Antiepileptic Therapy

An embodiment of the invention pertains to a method for delivering the antiepileptic drug phenytoin orally to a patient in need of antiepileptic therapy, which method comprises the steps of: (a) admitting into the patient a dosage form comprising: (1) an antiepileptic phenytoin composition comprising 1 to 750 mg of phenytoin; (2) a push layer comprising means for imbibing fluid for expanding and pushing the antiepileptic phenytoin from the dosage form; (3) an internal wall permeable to the passage of fluid for maintaining the structural integrity of the dosage form, and concomitantly protect the phenytoin from the gastric environment and thereby maintaining the pH of the sodium phenytoin in the dosage form for administering as the protected pH, which internal wall surrounds the phenytoin composition and the push composition; (4) a semipermeable wall that surrounds the internal wall, which semipermeable wall is permeable to the passage of fluid and impermeable to the passage for antiepileptic phenytoir; and (5) a passageway in the dosage form for delivering the antiepileptic phenytoin from the dosage form; (b) imbibing fluid through the semipermeable wall at a rate determined by the permeability of the semipermeable wall and the osmotic pressure gradient across the semipermeable wall then through the internal wall into the dosage form, thereby causing the push composition to expand; and (c) deliver the antiepileptic phenytoin through the passageway from the dosage form at a rate of 0.1 to 50 mg/hr over the therapeutic period to the patient to provide a blood plasma level of 2.5 to 20 μg/ml for the treatment of epilepsies.

The invention provides also a method for treating the symptoms of epilepsy by administering orally to a patient exhibiting the symptoms of epilepsy a sustained release dosage form that administers the following amounts of sodium phenytoin from a dosage form containing 30 mg of sodium phenytoin: 0–6 mg of phenytoin in 0–2 hrs, 1.5 to 12 mg of phenytoin in 0–4 hrs, 6 to 21 mg of phenytoin in 0–6 hrs, 9 to 30 mg of phenytoin in 0–8 hrs, 12 to 30 mg of phenytoin in 0–10 hrs, and 15 to 30 mg of phenytoin in 0–16 hrs. The invention provides further, a method for treating epilepsy in a epileptic patient by administering orally to the patient a sustained release dosage form that administers 0 to 3 mg in the first hour, 1 to 5 mg in the second hour, 1 to 5 mg in the third hour, 1 to 5 mg in the fourth hour, 1 to 7 mg in the fifth hour, 1 to 7 mg in the sixth hour, 1 to 7 mg in the seventh hour, 0 to 5 mg in the eighth hour, 0 to 3 mg in the ninth hour, 1 to 10 mg in the tenth hour, 0 to 3 mg in the eleventh hour and 0 to 3 mg in the twelfth hour.

The invention provides also a method for treating the symptoms of epilepsy by administering orally to a patient exhibiting the symptoms of epilepsy a sustained release dosage form that administers the following amounts of sodium phenytoin from a dosage form containing 100 mg of sodium phenytoin: 0–20 mg of phenytoin in 0–2 hrs, 5 to 40 mg of phenytoin in 0–4 hrs, 20 to 70 mg of phenytoin in 0–6 hrs, 30 to 100 mg of phenytoin in 0–8 hrs, 40 to 100 mg of phenytoin in 0–10 hrs and 50 to 100 mg of phenytoin in 0–12 hrs. The invention provides further, a method for treating epilepsy in a epileptic patient by administering orally to the patient a sustained release dosage form that administers 0 to 3 mg in the first hour, 5 to 12 mg in the second hour, 6 to 12 mg in the third hour, 6 to 12 mg in the fourth hour, 7 to 16 mg in the fifth hour, 7 to 16 mg in the sixth hour, 7 to 16 mg in the seventh hour, 6 to 13 mg in the eighth hour, 3 to 10 mg in the ninth hour, 1 to 10 mg in the tenth hour, 0 to 10 mg in the eleventh hour and 0 to 10 mg in the twelfth hour.

The invention provides also a method for treating the symptoms of epilepsy by administering orally to a patient exhibiting the symptoms of epilepsy a sustained release dosage form that administers the following amounts of sodium phenytoin from a dosage form containing 300 mg of sodium phenytoin: 0–60 mg of phenytoin in 0–2 hrs, 15 to 105 mg of phenytoin in 0–4 hrs, 60 to 210 mg of phenytoin in 0–6 hrs, 90 to 300 mg of phenytoin in 0–8 hrs, 120 to 300 mg of phenytoin in 0–10 hrs and 150 to 300 mg of phenytoin in 0–12 hrs. The invention provides further, a method for treating epilepsy in a epileptic patient by administering orally to the patient a sustained release dosage form that administers 0 to 20 mg in the first hour, 5 to 30 mg in the second hour, 10 to 30 mg in the third hour, 15 to 45 mg in the fourth hour, 15 to 45 mg in the fifth hour, 15 to 45 mg in the sixth hour, 20 to 60 mg in the seventh hour, 20 to 60 mg in the eighth hour, 10 to 40 mg in the ninth hour, 10 to 40 mg in the tenth hour, 0 to 30 mg in the eleventh hour and 0 to 30 mg in the twelfth hour.

In summary, it will be appreciated that the present invention contributes to the antiepileptic art an unobvious dosage form that possesses a practical utility: administering an antiepileptic drug in a prompt dose and in a known dose released per unit time over time. While the invention has been described and pointed out in detail with reference to operative embodiments thereof, it will be understood to those skilled in the antiepileptic art that various changes, modifications, substitutions and omissions can be made without departing from the spirit of the invention. It is intended, therefore, that the invention embrace those equivalents within the scope of the claims that follow.

What is claimed is:

1. A method for the therapeutic management of epilepsy, wherein the method comprises administering orally to a patient having epilepsy a therapeutically-effective amount of a composition comprising phenytoin, a polyethylene oxide, and tromethamine over an extended-dosing time.

2. The method of claim 1 treating epilepsy, wherein the method comprises administering to an epileptic patient orally an extended-release dose of phenytoin to produce a blood-plasma concentration of 0.1 to 20 µg/ml of phenytoin for treating the epilepsy.

3. The method of claim 1 for treating epilepsy, wherein the method comprises administering to a patient orally an extended release dose of 1 mg to 750 mg of phenytoin at a rate of 0.04 mg/hr to 50 mg/hr.

4. The method of claim 1 for treating the symptoms of epilepsy in a patient having the symptoms of epilepsy, wherein the method comprises administering orally an extended-release dose of phenytoin to produce a blood-plasma concentration of 0.1 to 20 µg/ml of phenytoin accompanied by a member selected from the group consisting of phenobarbitone, carbamazepine, primidone, felbamate, gabapentin, mephenytoin, ethytoin, and phenobarbitol.

* * * * *